(12) United States Patent
Baunoch et al.

(10) Patent No.: US 11,746,371 B2
(45) Date of Patent: Sep. 5, 2023

(54) METHODS FOR TREATING POLYMICROBIAL INFECTIONS

(71) Applicant: CAP DIAGNOSTICS, LLC, Irvine, CA (US)

(72) Inventors: David A. Baunoch, Irvine, CA (US); Miguel F. R. Penaranda, Irvine, CA (US); Michael L. Opel, Irvine, CA (US); Maher Badir, Irvine, CA (US); Natalie Luke, Irvine, CA (US)

(73) Assignee: CAP DIAGNOSTICS, LLC, Irvine, CA (US)

( * ) Notice: Subject to any disclaimer, the term of this patent is extended or adjusted under 35 U.S.C. 154(b) by 101 days.

(21) Appl. No.: 17/335,767

(22) Filed: Jun. 1, 2021

(65) Prior Publication Data

US 2021/0301315 A1 Sep. 30, 2021

Related U.S. Application Data

(60) Division of application No. 16/848,651, filed on Apr. 14, 2020, now Pat. No. 11,053,532, which is a (Continued)

(51) Int. Cl.
*C12Q 1/14* (2006.01)
*C12Q 1/08* (2006.01)
*G01N 21/59* (2006.01)

(52) U.S. Cl.
CPC .............. *C12Q 1/08* (2013.01); *G01N 21/59* (2013.01); *G01N 21/5907* (2013.01); *G01N 2021/593* (2013.01)

(58) Field of Classification Search
CPC ........................................................ C12Q 1/14
See application file for complete search history.

(56) References Cited

U.S. PATENT DOCUMENTS 3,855,197 A 12/1974 Hirsch et al.
4,132,599 A 1/1979 Picciolo et al.
(Continued)

FOREIGN PATENT DOCUMENTS

EP 2521459 T3 6/2010
JP 2012-518427 A 8/2012
(Continued)

OTHER PUBLICATIONS

Ma et al. "Antibiotic susceptibility of coagulase-negative staphylococci (CoNS): emergence of teicoplanin-non-susceptible CoNS strains with inducible resistance to vancomycin," J Med Microbiol, Jul. 28, 2011 (Jul. 28, 2011), vol. 60, pp. 1661-1668.
(Continued)

*Primary Examiner* — Rosanne Kosson
(74) *Attorney, Agent, or Firm* — NGUYEN TARBET LLC

(57) ABSTRACT

Methods for detecting and treating polymicrobial infections, wherein a mixed population of microbes (e.g., bacteria) are present in a patient sample and the microbes are not first isolated from the sample. For example, the present invention describes specific polymicrobial infections and methods of treating said infections, wherein a particular antibiotic or a group of antibiotics are selected based on the composition of the polymicrobial infections.

4 Claims, 10 Drawing Sheets
(8 of 10 Drawing Sheet(s) Filed in Color)

Related U.S. Application Data continuation-in-part of application No. 16/216,751, filed on Dec. 11, 2018, now abandoned, which is a continuation of application No. 15/957,780, filed on Apr. 19, 2018, now Pat. No. 10,160,991.

(60) Provisional application No. 63/009,337, filed on Apr. 13, 2020, provisional application No. 62/988,186, filed on Mar. 11, 2020, provisional application No. 62/978,149, filed on Feb. 18, 2020, provisional application No. 62/977,637, filed on Feb. 17, 2020, provisional application No. 62/956,923, filed on Jan. 3, 2020, provisional application No. 62/928,815, filed on Oct. 31, 2019, provisional application No. 62/924,614, filed on Oct. 22, 2019, provisional application No. 62/487,395, filed on Apr. 19, 2017.

(56) References Cited

U.S. PATENT DOCUMENTS

| | | |
|---|---|---|
| 6,027,734 A | 2/2000 | Briles et al. |
| 6,294,177 B1 | 9/2001 | Fattom |
| 7,384,778 B2 | 6/2008 | Chen et al. |
| 7,648,707 B2 | 1/2010 | Pillich et al. |
| 8,518,416 B2 | 8/2013 | Pillich et al. |
| 9,511,101 B2 | 12/2016 | Pillich et al. |
| 9,834,808 B2 | 12/2017 | Stern et al. |
| 10,160,991 B2 | 12/2018 | Baunoch et al. |
| 2004/0005653 A1 | 1/2004 | Chen et al. |
| 2005/0095665 A1 | 5/2005 | Williams et al. |
| 2008/0132457 A1 | 6/2008 | Bostian et al. |
| 2009/0291854 A1 | 11/2009 | Wiesinger-Mayr et al. |
| 2012/0076819 A1 | 3/2012 | Pillich et al. |
| 2013/0029981 A1 | 1/2013 | De Keersmaecker et al. |
| 2013/0095167 A1* | 4/2013 | Warnke ............... A61L 27/60 977/788 |
| 2015/0247177 A1 | 9/2015 | Orenga et al. |
| 2016/0289729 A1 | 10/2016 | Richards et al. |
| 2018/0135108 A1 | 5/2018 | Etchebarne |
| 2018/0237829 A1 | 8/2018 | Fry et al. |
| 2018/0305730 A1 | 10/2018 | Baunoch et al. |
| 2018/0307795 A1 | 10/2018 | Sohn et al. |
| 2019/0153501 A1 | 5/2019 | Baunoch et al. |
| 2020/0347433 A1 | 11/2020 | Baunoch et al. |

FOREIGN PATENT DOCUMENTS

| | | |
|---|---|---|
| WO | WO2005089738 A2 | 9/2005 |
| WO | WO2010097683 A2 | 9/2010 |
| WO | WO2013166460 A1 | 11/2013 |
| WO | WO2015042583 A2 | 3/2015 |
| WO | WO2015189390 A1 | 12/2015 |
| WO | WO2016207065 A1 | 12/2016 |
| WO | WO2018195343 A1 | 10/2018 |

OTHER PUBLICATIONS

Alpay et al. "Urinary tract infections in the geriatric patients." Pakistan journal of medical sciences 34.1 (2018): 67.

Simmering, Jacob E., et al. "The increase in hospitalizations for urinary tract infections and the associated costs in the United States, 1998-2011." Open forum infectious diseases. vol. 4. No. 1. Oxford University Press, 2017.

Daly et al. "Utilization of M-PCR and P-AST for diagnosis and management of urinary tract infections in home-based primary care." JOJ Uro Nephron 7.2 (2020): 555707.

Price et al. "Urine trouble: should we think differently about UTI?." International urogynecology journal 29.2 (2018): 205-210.

Fajardo et al. "The neglected intrinsic resistome of bacterial pathogens." PloS one 3.2 (2008): e1619.

Bismuth et al. "Gene heterogeneity for tetracycline resistance in Staphylococcus spp." Antimicrobial Agents and Chemotherapy 34.8 (1990): 1611-1614.

Van Hoek et al. "Acquired antibiotic resistance genes: an overview." Frontiers in microbiology 2 (2011): 203.

Girgis et al. "Genetic architecture of intrinsic antibiotic susceptibility." PloS one 4.5 (2009): e5629.

Suzuki et al. "Prediction of antibiotic resistance by gene expression profiles." Nature communications 5.1 (2014): 1-12.

Duran et al. "Antibiotic resistance genes & susceptibility patterns in staphylococci." The Indian journal of medical research 135.3 (2012): 389.

Baunoch et al. "Multisite Prospective Comparison of Multiplex Polymerase Chain Reaction Testing with Urine Culture for Diagnosis of Urinary Tract Infections in Symptomatic Patients" Journal of Surgical Urology. (2020).

Vollstedt et al. "Bacterial interactions as detected by Pooled Antibiotic Susceptibility Testing (P-AST) in polymicrobial urine specimens." J Sur Urol (2020).

Rivoarilala et al. "Rapid in vitro detection of CTX-M groups 1, 2, 8, 9 resistance genes by LAMP assays." PloS one 13.7 (2018): e0200421.

Chérif et al. "Cooccurrence of Multiple AmpC β-Lactamases in Escherichia coli, Klebsiella pneumoniae, and Proteus mirabilis in Tunisia." Antimicrobial agents and chemotherapy 60.1 (2016): 44-51.

Queenan, Anne Marie, and Karen Bush. "Carbapenemases: the versatile β-lactamases." Clinical microbiology reviews 20.3 (2007): 440-458.

Bauerfeind et al. "A novel type of AmpC β-lactamase, ACC-1, produced by a Klebsiella pneumoniae strain causing nosocomial pneumonia." Antimicrobial agents and chemotherapy 43.8 (1999): 1924-1931.

Tran, John H., and George A. Jacoby. "Mechanism of plasmid-mediated quinolone resistance." Proceedings of the National Academy of Sciences 99.8 (2002): 5638-5642.

Matthew, M., R. W. Hedges, and J. T. Smith. "Types of beta-lactamase determined by plasmids in gram-negative bacteria." Journal of Bacteriology 138.3 (1979): 657-662.

Negri et al. "Concentration-dependent selection of small phenotypic differences in TEM β-lactamase-mediated antibiotic resistance." Antimicrobial agents and chemotherapy 44.9 (2000): 2485-2491.

Courvalin, Patrice. "Vancomycin resistance in gram-positive cocci." Clinical infectious diseases 42.Supplement_1 (2006): S25-S34.

Kot, Barbara. "Antibiotic Resistance Among Uropathogenic." Polish journal of microbiology 68.4 (2019): 403-415.

Paul, Rudrajit. "State of the globe: Rising antimicrobial resistance of pathogens in urinary tract infection." Journal of Global Infectious Diseases 10.3 (2018): 117.

Baerheim, Anders. "Empirical treatment of uncomplicated cystitis: Keep it simple." BMJ 323.7323 (2001): 1197-1198.

Liu, Bo, and Mihai Pop. "ARDB—antibiotic resistance genes database." Nucleic acids research 37.suppl_1 (2009): D443-D447.

Alcock et al. "CARD 2020: antibiotic resistome surveillance with the comprehensive antibiotic resistance database." Nucleic acids research 48.D1 (2020): D517-D525.

Choi et al. "Multiplex PCR for the detection of genes encoding aminoglycoside modifying enzymes and methicillin resistance among Staphylococcus species." Journal of Korean medical science 18.5 (2003): 631-636.

Martineau et al. "Correlation between the resistance genotype determined by multiplex PCR assays and the antibiotic susceptibility patterns of Staphylococcus aureus and Staphylococcus epidermidis." Antimicrobial agents and chemotherapy 44.2 (2000): 231-238.

Kime et al. "Transient silencing of antibiotic resistance by mutation represents a significant potential source of unanticipated therapeutic failure." MBio 10.5 (2019): e01755-19.

Cabot et al. "Overexpression of AmpC and efflux pumps in Pseudomonas aeruginosa isolates from bloodstream infections: prevalence and impact on resistance in a Spanish multicenter study." Antimicrobial agents and chemotherapy 55.5 (2011): 1906-1911.

Lee et al." I he impact of the increased use of piperacillin/tazobactam on the selection of antibiotic resistance among invasive

(56) References Cited

OTHER PUBLICATIONS

*Escherichia coli* and Klebsiella pneumoniae isolates." International Journal of Infectious Diseases 17.8 (2013): e638-e643.

Flentie et al. "Microplate-based surface area assay for rapid phenotypic antibiotic susceptibility testing." Scientific reports 9.1 (2019): 1-9.

Liu et al. "Expressing urine from a gel disposable diaper for biomonitoring using phthalates as an example." Journal of Exposure Science & Environmental Epidemiology 22.6 (2012): 625-631.

Davenport et al. "New and developing diagnostic technologies for urinary tract infections." Nature Reviews Urology 14.5 (2017): 296-310.

Mohan et al., A microfluidic approach to study the effect of bacterial interactions on antimicrobial susceptibility in polymicrobial cultures, RSC Advances, vol. 5, 2015 [retrieved on Jun. 8, 2018].

Sun et al., Rapid antimicrobial susceptibility test for identification of new therapeutics and drug combinations against multidrug-resistant bacteria, Emerging Microbes & infections. vol. 5, Nov. 9, 2016 [retrieved on Jun. 8, 2018].

Emilie Weibull et al.: Bacterial Nanoscale Cultures for Phenotypic Multiplexed Antibiotic Susceptibility Testing, Journal of Clinical Microbiology, vol. 52, No. 9, Jul. 2, 2014 (Jul. 2, 2014), pp. 3310-3317.

Ritika Mohan et al: "A microfluidic approach to study the effect of bacterial interactions on antimicrobial susceptibility in polymicrobial cultures" RSC Advances, vol. 5, No. 44, Jan. 1, 2015 pp. 35211-35223.

Coorevits L et al: "Direct susceptibility testing by disk diffusion on clinical samples: a rapid and accurate tool for antibiotic stewardship", European Journal of Clinical Microbiology & Infectious Diseases, Springer, Wiesbaden, DE, vol. 34, No. 6, Feb. 20, 2015, pp. 1207-1212.

Christina Chantell: "Multiplexed Automated Digital Microscopy for Rapid Identification and Antimicrobial Susceptibility Testing of Bacteria and Yeast Directly from Clinical Samples", Clinical Microbiology Newsletter, vol. 37, No. 20, Oct. 1, 2015, pp. 161-167.

Lavigne et al., "Virulent synergistic effect between Enterococcus faecalis and *Escherichia coli* assayed by using the Caenorhabditis elegans model," PLoS One 3(10): 1-5, 2008.

International Search Report and Written Opinion mailed on Jul. 16, 2018 for International Application No. PCT/US2018/028422 filed on Apr. 19, 2018.

Shahidi A. and Ellner P.D. "Effect of Mixed Cultures on Antibiotic Susceptibilty Testing," Applied Microbiology 18:766-770, 1969.

Guidance for Industry and FDA. Class II Special Controls Guidance Document: Antimicrobial Susceptibility Test (AST) Systems. US Department of Health and Human Services, Food and Drug Administration, Center for Devices and Radiological Health, Bacteriology Branch, Division of Microbiology Devices, Office of In Vitro Diagnostic Device (OIVD) Evaluation and Safety. Aug. 28, 2009.

Procedures/Guidelines for the Microbiology Laboratory, College of Physicians & Surgeons of Saskatchewan Laboratory Quality Assurance Program. 2016.

Gundersen Health System Standard Operating Procedure. Vitek 2 Compact—Identification and Susceptibility Testing. https://www.gundersenhealth.org/app/files/public/6557/Lab-Policies-Vitek-2-Compact-Identification-and-Susceptibility-Testing-Lab-1512.pdf. Jan. 5, 2018.

College of American Pathologies, Microbiology Checklist, Aug. 21, 2017.

Dijkshoorn L et al. "Strain, clone and species: comments on the three basic concepts of bacteriology," J. Med. Microbiol. 49:397-401, 2000.

Tally, "Factors affecting the choice of antibiotics in mixed infections," J Antimicrobial Chemotherapy 22(Suppl. A):87-100, 1988.

El-Azizi, "Novel microdilution method to assess double and triple antibiotic combination therapy in vitro," Int J Microbial, Hindawi Publishing Corp., article No. 4612021, Mar. 29, 2016.

Alteri et al. "Preferential Use of Central Metabolism In Vivo Reveals a Nutritional Basis for Polymicrobial Infection" PLOS Pathogens, Jan. 2015 I vol. 11 I Issue 1.

Croxall et al. "Increased human pathogenic potential of *Escherichia coli* from polymicrobial urinary tract infections in comparison to isolates from monomicrobial culture samples" Journal of Medical Microbiology (2011 ), 60, 102-109.

Hollick et al. "Comparison of Direct and Standardized Disk Diffusion Susceptibility Testing of Urine Cultures" Antimicrobial Agiints and Chemotherapy, May 1976, p. 804-809.

Johnson et al. "Direct Antimicrobial Susceptibility Testing for Acute Urinary Tract Infections in Women" Journal of Clinical Microbiology, Sep. 1995, p. 2316-2323.

Kline et al. "Gram-Positive Uropathogens, Polymicrobial Urinary Tract Infection, and the Emerging Microbiota of the Urinary Tract" Microbial Spectr. Apr. 2016; 4(2):1-54.

Cockerill et al "Methods for Dilution Antimicrobial Susceptibility Tests for Bacteria That Grow Aerobically; Approved Standard-Ninth Edition" Jan. 2012.

Wolfe et al. "Evidence of Uncultivated Bacteria in the Adult Female Bladder" Apr. 2012, Journal of Clinical Microbiology p. 1376-1383.

\* cited by examiner

| Class | Antibiotic | Additive Effects Interactions | Highest Single-Agent Interactions | | Union Principle Interactions | |
|---|---|---|---|---|---|---|
| Penicillins | Ampicillin | | | | | |
| | Amoxicillin-Clavulanate | | | Increase Resistance | Decrease Resistance | E. coli & CNS |
| | Ampicillin/Sulbactam | | E. coli & Klebsiella | Increase Resistance | | |
| Cephalosporins | Cefaclor | Increase Resistance | E. coli & Klebsiella | Decrease Resistance | Decrease Resistance | Klebsiella & Pseudomonas |
| | Cefazolin | Increase Resistance | E. coli & Klebsiella | Decrease Resistance | Decrease Resistance | Klebsiella & Pseudomonas |
| | Cefepime | Increase Resistance | E. coli & Klebsiella | Decrease Resistance | Decrease Resistance | P. mirabilis & Klebsiella |
| | | | E. coli & Proteus | | | |
| | Cefoxitin | Increase Resistance | E. coli & Klebsiella | Decrease Resistance | Decrease Resistance | Pseudomonas & Klebsiella |
| | Ceftazidime | Increase Resistance | E. coli & Klebsiella | Decrease Resistance | Decrease Resistance | Pseudomonas & Klebsiella |
| | | | E. coli & Pseudomonas | | | |
| | Ceftriaxone | Increase Resistance | E. coli & Klebsiella | Klebsiella & CNS | Decrease Resistance | Klebsiella & CNS |
| | | | | E. coli & CNS | | E. coli & CNS |
| | | | | Decrease Resistance | | VGS & CNS |
| | | | | VGS & Klebsiella | | VGS & Klebsiella |
| | | | | E. coli & VGS | | E. coli & VGS |
| | | | | | | P. mirabilis & VGS |
| | | | | | | P. mirabilis & CNS |

FIG. 3

| Class | Antibiotic | Additive Effects Interactions | | Highest Single Agent Interactions | | Union Principle Interactions | |
|---|---|---|---|---|---|---|---|
| Fluoroquinolones | Ciprofloxacin | Decrease Resistance | Klebsiella & CNS | Decrease Resistance | Klebsiella & CNS | Decrease Resistance | Klebsiella & CNS |
| | | | A. schaalii & E. coli | | A. schaalii & Klebsiella | | A. schaalii & Klebsiella |
| | | | | | | | E. coli & CNS |
| | | | | | | | E. coli & VGS |
| | | | A. schaalii & CNS | | | | A. schaalii & CNS |
| | | Increase Resistance | E. coli & Klebsiella | | A. schaalii & VGS | | A. schaalii & VGS |
| | | | | | | | A. schaalii & E. coli |
| | Levofloxacin | Decrease Resistance | Klebsiella & CNS | Decrease Resistance | Klebsiella & CNS | Decrease Resistance | Klebsiella & CNS |
| | | | | | | | A. schaalii & Klebsiella |
| | | | A. schaalii & E. coli | | | | E. coli & VGS |
| | | | A. schaalii & E. coli | | | | CNS & VGS |
| | | Increase Resistance | E. coli & Klebsiella | | A. schaalii & VGS | | A. schaalii & VGS |
| | | | | | | | A. schaalii & VGS |
| | | | | | | | A. schaalii & E. coli |
| Aminoglycoside | Gentamicin | | | Decrease Resistance | | Decrease Resistance | Klebsiella & E. coli |
| | Meropenem | Increase Resistance | E. coli & Klebsiella | Decrease Resistance | E. coli & E. faecalis | Decrease Resistance | E. coli & E. faecalis |
| | | | | | E. faecalis & Klebsiella | | E. faecalis & Klebsiella |
| | | | | | Pseudomonas & Klebsiella | | Pseudomonas & Klebsiella |
| | | | | | Pseudomonas & P. mirabilis | | Pseudomonas & P. mirabilis |
| | | | | | P. mirabilis & E. faecalis | | P. mirabilis & E. faecalis |
| | | | | | | | P. mirabilis & Klebsiella |
| | Nitrofurantoin | | | | | | |
| Glycopeptide | Vancomycin | Increase Resistance | | Decrease Resistance | | Decrease Resistance | CNS & VGS |
| | | | | | | | E. faecalis & VGS |
| Tetracycline | Tetracycline | Decrease Resistance | E. faecalis & Klebsiella | Decrease Resistance | E. faecalis & Klebsiella | Decrease Resistance | E. faecalis & Klebsiella |
| | | Increase Resistance | CNS & Klebsiella | | | | CNS & E. faecalis |
| Combo | Trimethoprim/Sulfamethoxazole | | | | | | |
| B Lactamase Inhibitor | Piperacillin/Tazobactam | | | | | | |

| Class | Antibiotic | Unadjusted Odds Ratio (95% CI) | p-value | Adjusted Odds Ratio (95% CI) | p-value |
|---|---|---|---|---|---|
| Penicillins | Ampicillin | 1.37 (1.10, 1.70) | 0.005 | 1.14 (1.05, 1.24) | 0.001 |
| | Amoxicillin/Clavulanate | 1.38 (1.09, 1.74) | 0.008 | 1.16 (1.07, 1.26) | 0.0005 |
| | Ampicillin/Sulbactam | N.S. | N.S. | N.S. | N.S. |
| Cephalosporins | Cefaclor | 1.42 (1.15, 1.77) | 0.001 | 1.15 (1.06, 1.25) | 0.0006 |
| | Cefazolin | 1.38 (1.11, 1.72) | 0.004 | 1.15 (1.06, 1.25) | 0.0004 |
| | Cefepime | 1.45 (1.16, 1.80) | 0.003 | 1.12 (1.03, 1.21) | 0.006 |
| | Cefoxitin | 1.41 (1.14, 1.76) | 0.002 | 1.10 (1.01, 1.19) | 0.02 |
| | Ceftazidime | 1.31 (1.05, 1.62) | 0.02 | N.S. | N.S. |
| | Ceftriaxone | 1.25 (1.01, 1.56) | 0.04 | 1.09 (1.01, 1.18) | 0.03 |
| Fluoroquinolones | Ciprofloxacin | N.S. | N.S. | N.S. | N.S. |
| | Levofloxacin | N.S. | N.S. | N.S. | N.S. |
| Aminoglycosides | Gentamicin | N.S. | N.S. | N.S. | N.S. |
| Carbapenems | Meropenem | N.S. | N.S. | N.S. | N.S. |
| | Nitrofurantoin | N.S. | N.S. | N.S. | N.S. |
| Glycopeptides | Vancomycin | 2.15 (1.63, 2.84) | <0.0001 | 1.38 (1.21, 1.56) | <0.0001 |
| Tetracycline | Tetracycline | 1.26 (1.02, 1.57) | 0.04 | 1.11 (1.02, 1.20) | 0.01 |
| Sulfonamides | Trimethoprim/Sulfamethoxazole | N.S. | N.S. | N.S. | N.S. |
| Beta Lactamase inhibitors | Piperacillin/Tazobactam | N.S. | N.S. | 0.75 (0.61, 0.94) | 0.01 |

FIG. 6

| Class | Antibiotic | Bacteria with high resistance rates (odds-ratio) | Bacteria with low resistance rates (odds-ratio) | Additive Effects Interactions | Highest Single Agent Interactions | Union Principle Interactions |
|---|---|---|---|---|---|---|
| Penicillins | Ampicillin | Corynebacterium riegelii (2.1) E. coli (2.0) Klebsiella pneumonia * (3.3) Pseudomonas aeruginosa * (25.1) Proteus mirabilis (1.4) | CNS (0.60) | CNS & Klebsiella together decrease the odds of resistance | CNS & Klebsiella together decrease resistance | CNS & Klebsiella together decrease resistance, E. coli & P. mirabilis and Pseudomonas & P. mirabilis decrease resistance |
| | Amoxicillin/ Clavulanate | Actinobaculum schaallii (1.5) E. coli (1.3) Proteus mirabilis (2.2) Pseudomonas aeruginosa * (23.4) | CNS (0.71) | | A. schaalli & Pseudomonas decrease resistance | CNS & A. schaalli and E. coli & CNS decrease resistance |
| | Ampicillin/ Sulbactam | E. coli (2.0) Klebsiella pneumonia (1.6) Pseudomonas aeruginosa * (13.0) | | | E. coli & Klebsiella together increase resistance | |
| Cephalosporins | Cefaclor | E. faecalis & (2.3) Pseudomonas aeruginosa (8.6) | Klebsiella pneumonia (0.69) | Klebsiella & E. faecalis together decrease the odds of resistance; E. coli & Klebsiella together increase the odds of resistance | Klebsiella & E. faecalis and E. coli & E. faecalis and Klebsiella & Pseudomonas together decrease resistance | Klebsiella & E. faecalis and E. coli & E. faecalis and Klebsiella & Pseudomonas together decrease resistance |
| | Cefazolin | Actinobaculum schaallii (1.3) Pseudomonas aeruginosa (2.2) | | Pseudomonas & E. faecalis together decrease the odds of resistance; E. coli & Klebsiella together increase the odds of resistance | E. faecalis & A. schaalli together increase resistance; Klebsiella & A. schaalli and E. coli & A. schaalli and Klebsiella & Pseudomonas together decrease resistance | E. faecalis & E. coli and Klebsiella & A. schaalli and E. coli & A. schaalli and Klebsiella & Pseudomonas together decrease resistance |
| | Cefepime | E. faecalis & (9.4) E. coli (1.7) | | E. coli & Klebsiella and E. coli & Proteus together increase the odds of resistance | Klebsiella & E. faecalis and E. coli & E. faecalis and P. mirabilis & E. faecalis and P. mirabilis & Klebsiella together decrease resistance | Klebsiella & E. faecalis and E. coli & E. faecalis and P. mirabilis & Klebsiella together decrease resistance |

FIG. 7

| Class | Antibiotic | Bacteria with high resistance rates (odds-ratio) | Bacteria with low resistance rates (odds-ratio) | Additive Effects Interactions | Highest Single Agent Interactions | Union Principle Interactions |
|---|---|---|---|---|---|---|
| | Cefoxitin | | | Pseudomonas & E. faecalis together decrease the odds of resistance; E. coli & Klebsiella together increase the odds of resistance | Klebsiella & E. faecalis and E. coli & E. faecalis and Pseudomonas & Klebsiella together decrease resistance | Klebsiella & E. faecalis and E. coli & E. faecalis and Pseudomonas & Klebsiella together decrease resistance |
| | Ceftazidime | E. faecalis & (7.3) | Klebsiella pneumonia (0.53) | CNS & Klebsiella together decrease the odds of resistance; E. coli & Klebsiella and E. coli & Pseudomonas together increase the odds of resistance | Klebsiella & CNS and E. coli & CNS and Pseudomonas & CNS and E. faecalis & Klebsiella and Pseudomonas & Klebsiella and E. coli & E. faecalis together decrease resistance; E. faecalis & CNS together increase resistance | Klebsiella & CNS and E. coli & CNS and Pseudomonas & CNS and E. faecalis & Klebsiella and Pseudomonas & Klebsiella and E. coli & E. faecalis together decrease resistance |
| | Ceftriaxone | E. faecalis & (6.9) | Klebsiella pneumonia (0.65) Proteus mirabilis (0.41) VGS (0.73) | Pseudomonas & CNS together decrease the odds of resistance; E. coli & Klebsiella together increase the odds of resistance | Klebsiella & CNS and E. coli & CNS and VGS & CNS and E. faecalis & Klebsiella and Pseudomonas & Klebsiella and VGS & Klebsiella and E. coli & E. faecalis together decrease resistance; E. faecalis & CNS and E. coli and P. mirabilis together increase resistance | Klebsiella & CNS and E. coli & CNS and VGS & CNS and E. faecalis & Klebsiella and Pseudomonas & Klebsiella and VGS & Klebsiella and E. coli & E. faecalis and E. coli and VGS and E. faecalis & VGS and P. mirabilis & VGS together decrease resistance |
| Fluoroquinolones | Ciprofloxacin | E. coli (1.5) | Klebsiella pneumonia (0.53) VGS (0.73) | Klebsiella & CNS and A. schaalii & E. coli and A. schaalii & CNS together decrease the odds of resistance; E. coli & Klebsiella together increase the odds of resistance | Klebsiella & CNS and A. schaalii & Klebsiella together decrease resistance | Klebsiella & CNS and A. schaalii & Klebsiella and A. schaalii & CNS and A. schaalii & E. coli together decrease resistance |
| | Gentamicin | E. faecalis (2.7) | E. coli (0.66) Klebsiella pneumonia (0.44) | | | Klebsiella & E. coli and Klebsiella & E. faecalis together decrease resistance |
| | Levofloxacin | E. coli (1.6) | Klebsiella pneumonia (0.61) VGS (0.73) | Klebsiella & CNS and A. schaalii & E. coli and A. schaalii & CNS together decrease the odds of resistance; E. coli & Klebsiella together increase the odds of resistance | Klebsiella & CNS and A. schaalii & Klebsiella together decrease resistance | Klebsiella & CNS and A. schaalii & CNS and A. schaalii & Klebsiella and A. schaalii & E. coli and VGS & E. coli and VGS & A. schaalii together decrease resistance |

FIG. 8

| Class | Antibiotic | Bacteria with high resistance rates (odds-ratio) | Bacteria with low resistance rates (odds-ratio) | Additive Effects Interactions | Highest Single Agent Interactions | Union Principle Interactions |
|---|---|---|---|---|---|---|
| Carbapenem | Meropenem | E. faecalis (6.6) | Alloscardovia omnicolens (0.50) Pseudomonas aeruginosa (0.43) | E. coli & A. omnicolens together decrease the odds of resistance; E. coli & Proteus and E. coli & Klebsiella together increase the odds of resistance | E. coli & A. omnicolens and E. coli & E. faecalis and E. faecalis & Klebsiella and Pseudomonas & Klebsiella and Pseudomonas & P. mirabilis and P. mirabilis & E. faecalis together decrease resistance | E. coli & A. omnicolens and E. coli & E. faecalis and E. coli & Pseudomonas and E. faecalis & Klebsiella and Pseudomonas & Klebsiella and Pseudomonas & P. mirabilis and P. mirabilis & E. faecalis and P. mirabilis & Klebsiella together decrease resistance |
| | Nitrofurantoin | Pseudomonas aeruginosa (21.6) | E. coli (0.60) | | | |
| Glycopeptide | Vancomycin | Corynebacterium riegelii (3.3) E. coli * (2.0) Klebsiella pneumonia (2.2) Proteus mirabilis (26.3) Pseudomonas aeruginosa * (32.5) VGS (1.6) | CNS (0.72) | E. coli & Klebsiella together decrease the odds of resistance; CNS & E. faecalis together increase the odds of resistance; | CNS & VGS and E. faecalis & VGS decrease resistance | CNS & VGS and E. faecalis & VGS and E. faecalis & CNS decrease resistance |
| Tetracyclines | Tetracycline | Proteus mirabilis (3.8) Pseudomonas aeruginosa (1.3) Streptococcus agalactiae (1.6) | | E. faecalis & Klebsiella and E. faecalis & Proteus together decrease the odds of resistance; CNS & Klebsiella together increase the odds of resistance | E. faecalis & Klebsiella and Klebsiella & Pseudomonas together decrease resistance; Strep. agalactiae & E. faecalis together increase resistance | E. faecalis & Klebsiella and Klebsiella & Pseudomonas and Klebsiella & P. mirabilis and CNS & Pseudomonas and CNS & E. faecalis together decrease resistance; Strep. agalactiae & E. faecalis together increase resistance |
| | Trimethoprim/ Sulfa | E. faecalis (1.4) Pseudomonas aeruginosa (2.3) | Klebsiella pneumonia (0.62) | | E. faecalis & Klebsiella together decrease resistance | E. faecalis & Klebsiella and Klebsiella & Pseudomonas and E. faecalis & Pseudomonas together decrease resistance |
| | Piperacillin/ Tazobactam | | Actinobaculum schaalii (0.43) | | | |

| | 1 | 2 | 3 | 4 | 5 | 6 |
|---|---|---|---|---|---|---|
| A | No antibiotic | Mero (20) | Levo (40) | Ceftriaxone (640) | Pip/Tazo (640,40) | Tetra (160) |
| B | Nitro (320) | Mero (40) | Levo (80) | Vanco (20) | Pip/Tazo (1280,40) | Amp (80) |
| C | Nitro (640) | Mero (80) | Ceftriaxone (10) | Vanco (40) | Cefoxitin (40) | Amp (160) |
| D | Nitro (1280) | Amp/Sulb (80,40) | Ceftriaxone (20) | Vanco (80) | Cefoxitin (80) | Amp (320) |
| E | Cipro (10) | Amp/Sulb (160,80) | Ceftriaxone (40) | Vanco (160) | Cefoxitin (160) | TMP/SMX (20,380) |
| F | Cipro (20) | Amp/Sulb (320,160) | Ceftriaxone (80) | Vanco (320) | Cefoxitin (320) | TMP/SMX (40,760) |
| G | Cipro (40) | Levo (10) | Ceftriaxone (160) | Pip/Tazo (160,40) | Tetra (40) | AB-blend |
| h | Mero (10) | Levo (20) | Ceftriaxone (320) | Pip/Tazo (320,40) | Tetra (80) | empty |

FIG. 11

| | 1 | 2 | 3 | 4 | 5 | 6 | 7 | 8 |
|---|---|---|---|---|---|---|---|---|
| A | No-Antibiotic | Mero (80) | Ceftriaxone (40) | Pip/Tazo (160,40) | Tetra (160) | Cefazolin (160) | Ceftazidime (40) | No-Antibiotic |
| B | Nitro (320) | Amp/Sulb (80,40) | Ceftriaxone (80) | Pip/Tazo (1280,40) | Amp (80) | Cefazolin (320) | Ceftazidime (80) | No-Antibiotic |
| C | Nitro (1280) | Amp/Sulb (320,160) | Ceftriaxone (640) | Cefoxitin (40) | Amp (160) | Cefepime (10) | Ceftazidime (160) | Cefaclor (80) |
| D | Cipro (10) | Levo (10) | Vanco (10) | Cefoxitin (80) | Amp (320) | Cefepime (20) | Ceftazidime (320) | Cefaclor (320) |
| E | Cipro (40) | Levo (20) | Vanco (20) | Cefoxitin (320) | TMP/SMX (20,380) | Cefepime (40) | Gentamicin (40) | Na Azide |
| F | Mero (10) | Levo (40) | Vanco (40) | Tetra (20) | TMP/SMX (40,760) | Cefepime (80) | Gentamicin (160) | No-Antibiotic |
| G | Mero (20) | Levo (80) | Vanco (160) | Tetra (40) | Cefazolin (20) | Cefepime (160) | Amox/Clav (80,40) | No-Antibiotic |
| H | Mero (40) | Ceftriaxone (10) | Vanco (320) | Tetra (80) | Cefazolin (80) | Cefepime (320) | Amox/Clav (320,160) | No-Antibiotic |

FIG. 12

METHODS FOR TREATING POLYMICROBIAL INFECTIONS

CROSS-REFERENCES TO RELATED APPLICATIONS

This application is a Divisional and claims benefit of U.S. patent application Ser. No. 16/848,651 filed Apr. 14, 2020, which is a non-provisional and claims benefit of U.S. Patent Application No. 62/924,614 filed Oct. 22, 2019, U.S. Patent Application No. 62/928,815 filed Oct. 31, 2019, U.S. Patent Application No. 62/956,923 filed Jan. 3, 2020, U.S. Patent Application No. 62/977,637 filed Feb. 17, 2020, U.S. Patent Application No. 62/978,149 filed Feb. 18, 2020, U.S. Patent Application No. 62/988,186 filed Mar. 11, 2020, and U.S. Patent Application No. 63/009,337 filed Apr. 13, 2020, the specifications of which are incorporated herein in their entirety by reference.

U.S. patent application Ser. No. 16/848,651 filed Apr. 14, 2020 is a continuation-in-part and claims benefit of U.S. patent application Ser. No. 16/216,751 filed Dec. 11, 2018, which is a continuation and claims benefit of U.S. patent application Ser. No. 15/957,780 filed Apr. 19, 2018 (now U.S. Pat. No. 10,160,991), the specifications of which are incorporated herein in their entirety by reference. U.S. patent application Ser. No. 15/957,780 is a non-provisional and claims benefit of U.S. Patent Application No. 62/487,395, filed Apr. 19, 2017, the specifications of which are incorporated herein in their entirety by reference.

BACKGROUND OF THE INVENTION

Field of the Invention

The present application is related to polymicrobial infections, more particularly to polymicrobial infections and therapeutic solutions for treatment of said polymicrobial infections.

Background Art

Infectious diseases can affect multiple organs systems and are responsible for significant morbidity, mortality, and economic impact. Infectious agents most often present as a complex polymicrobial infections rather than as a single pathogen infection. Within the body, the pathogens of the polymicrobial infections coexist with each other and through bacterial interactions change both the type of antibiotics the organisms are susceptible and the level of antibiotics required to treat the infection.

It was surprisingly found that certain polymicrobial infections are associated with changes in resistance, e.g., decreases in resistance or increases in resistance, to particular antibiotics.

BRIEF SUMMARY OF THE INVENTION

Disclosed herein are methods for detecting polymicrobial infections, methods for treating polymicrobial infections, methods of guiding treatment of a polymicrobial infection, etc., wherein a mixed population of microbes (e.g., bacteria) are present in a patient sample and the microbes are not first isolated from the sample.

The present invention describes specific polymicrobial infections and methods of treating said infections by either killing the microbes or methods of inhibiting growth of one or more of the microbes in a polymicrobial infection (e.g., inducing a bacteriostatic state), wherein a particular antibiotic or a group of antibiotics are selected based on the particular organisms in the polymicrobial infections. As is described below, certain polymicrobial infections have a surprising increase or decrease in antibiotic resistance. For example, the present invention describes treating a polymicrobial infection with *Klebsiella pneumoniae* and coagulase-negative *Staphylococcus* (CoNS) with amoxicillin/clavulanate since it was surprisingly found that the a polymicrobial infection with both *Klebsiella pneumoniae* and coagulase-negative *Staphylococcus* (CoNS) has a reduced odds of resistance to amoxicillin/clavulanate.

The present invention also features methods for guiding the treatment of particular polymicrobial infections, e.g., methods for helping a physician or other healthcare provider choose an appropriate antibiotic for treating a polymicrobial infection. For example, the methods feature providing a physician or healthcare professional information (e.g., a report) about a polymicrobial infection, wherein the report provided includes the odds of resistance the particular polymicrobial infection has to one or more antibiotics. The information can help guide the physician in the decision-making process. Without this information, the physician or healthcare provider may choose an inappropriate antibiotic for the infection, e.g., an antibiotic that the polymicrobial infection has increased odds of resistance to. Or, in certain embodiments, the physician or healthcare may see that the polymicrobial infection has a decreased odds of resistance to a particular antibiotic that in the case of a monomicrobial infection would not be appropriate for use. Or, in certain embodiments, the physician may see that the polymicrobial infection is susceptible to a weaker antibiotic, whereas in the case of a monomicrobial infection he/she may have opted for a stronger antibiotic. This may provide the physician with a broader range of antibiotics from which to choose.

The methods described herein may feature administering an antimicrobial to the patient having or suspected of having a particular polymicrobial infection. In certain embodiments, the methods herein also include the step of detecting the presence of a particular combination of microbes in the polymicrobial infection, e.g., from a source of the infection from the patient.

*Klebsiella pneumoniae* and Coagulase-Negative *Staphylococcus* (CONS)

As previously discussed, the present invention features a method of treating a polymicrobial infection comprising *Klebsiella pneumoniae* and coagulase-negative *Staphylococcus* (CONS) (or a method of killing or inhibiting growth of *K. pneumoniae* and coagulase-negative *Staphylococcus* (CONS)), wherein the method comprises introducing amoxicillin/clavulanate to the *K. pneumoniae* and CoNS polymicrobial infection (e.g., administering amoxicillin/clavulanate to the patient having or suspected of having a polymicrobial infection with *K. pneumoniae* and CoNS), wherein *K. pneumoniae* and CoNS together have a decreased odds of resistance to amoxicillin/clavulanate.

The present invention also features a method of treating a polymicrobial infection comprising *K. pneumoniae* and coagulase-negative *Staphylococcus* (CONS) (or a method of killing or inhibiting growth of *K. pneumoniae* and coagulase-negative *Staphylococcus* (CONS)), wherein the method comprises introducing ceftriaxone to the *K. pneumoniae* and CoNS polymicrobial infection (e.g., administering ceftriaxone to the patient having or suspected of having a polymicrobial infection with *K. pneumoniae* and CoNS), wherein *K. pneumoniae* and CoNS together have a decreased odds of resistance to ceftriaxone.

The present invention also features a method of treating a polymicrobial infection comprising *K. pneumoniae* and coagulase-negative *Staphylococcus* (CoNS) (or a method of killing or inhibiting growth of *K. pneumoniae* and coagulase-negative *Staphylococcus* (CONS)), wherein the method comprises introducing ciprofloxacin to the *K. pneumoniae* and CoNS polymicrobial infection (e.g., administering ciprofloxacin to the patient having or suspected of having a polymicrobial infection with *K. pneumoniae* and CoNS), wherein *K. pneumoniae* and CoNS together have a decreased odds of resistance to ciprofloxacin.

The present invention also features a method of treating a polymicrobial infection comprising *K. pneumoniae* and coagulase-negative *Staphylococcus* (CoNS) (or a method of killing or inhibiting growth of *K. pneumoniae* and coagulase-negative *Staphylococcus* (CONS)), wherein the method comprises introducing levofloxacin to the *K. pneumoniae* and CoNS polymicrobial infection (e.g., administering levofloxacin to the patient having or suspected of having a polymicrobial infection with *K. pneumoniae* and CoNS), wherein *K. pneumoniae* and CoNS together have a decreased odds of resistance to levofloxacin.

The present invention also features a method of treating a polymicrobial infection comprising *K. pneumoniae* and coagulase-negative *Staphylococcus* (CONS) (or a method of killing or inhibiting growth of *K. pneumoniae* and coagulase-negative *Staphylococcus* (CoNS)), wherein the method comprises introducing gentamicin to the *K. pneumoniae* and CoNS polymicrobial infection (e.g., administering gentamicin to the patient having or suspected of having a polymicrobial infection with *K. pneumoniae* and CoNS), wherein *K. pneumoniae* and CoNS together have a decreased odds of resistance to gentamicin.

The present invention also features a method of treating a polymicrobial infection comprising *K. pneumoniae* and coagulase-negative *Staphylococcus* (CONS) (or a method of killing or inhibiting growth of *K. pneumoniae* and coagulase-negative *Staphylococcus* (CoNS)), wherein the method comprises introducing TMP/sulfamethoxazole to the *K. pneumoniae* and CoNS polymicrobial infection (e.g., administering TMP/sulfamethoxazole to the patient having or suspected of having a polymicrobial infection with *K. pneumoniae* and CoNS), wherein *K. pneumoniae* and CoNS together have a decreased odds of resistance to TMP/sulfamethoxazole.

Thus, the methods of the present invention also include treating a polymicrobial infection comprising *K. pneumoniae* and coagulase-negative *Staphylococcus* (CoNS) may comprise introducing (e.g., administering) one or more antimicrobials selected from: amoxicillin/clavulanate, ceftriaxone, ciprofloxacin, levofloxacin, gentamicin, or TMP/sulfamethoxazole.

The present invention also features a method of guiding treatment of a polymicrobial infection comprising *Klebsiella pneumoniae* and coagulase-negative *Staphylococcus* (CoNS). The method may comprise detecting the polymicrobial infection with *K. pneumoniae* and CoNS and providing a report showing one or more antibiotics to which *K. pneumoniae* and CoNS have increased and/or decreases resistance to. The report may help the physician choose an appropriate antibiotic to administer to the patient.

Coagulase-Negative *Staphylococcus* (CONS) and *S. agalactiae*

The present invention also features a method of treating a polymicrobial infection comprising *S. agalactiae* and coagulase-negative *Staphylococcus* (CoNS) (or a method of killing or inhibiting growth of *S. agalactiae* and coagulase-negative *Staphylococcus* (CoNS)), wherein the method comprises introducing ceftriaxone to the *S. agalactiae* and CoNS polymicrobial infection (e.g., administering ceftriaxone to the patient having or suspected of having a polymicrobial infection with *S. agalactiae* and CoNS), wherein S, *agalactiae* and CoNS together have a decreased odds of resistance to ceftriaxone.

The present invention also features a method of treating a polymicrobial infection comprising *S. agalactiae* and coagulase-negative *Staphylococcus* (CONS) (or a method of killing or inhibiting growth of *S. agalactiae* and coagulase-negative *Staphylococcus* (CoNS)), wherein the method comprises introducing ciprofloxacin to the *S. agalactiae* and CoNS polymicrobial infection (e.g., administering ciprofloxacin to the patient having or suspected of having a polymicrobial infection with *S. agalactiae* and CoNS), wherein *S. agalactiae* and CoNS together have a decreased odds of resistance to ciprofloxacin.

The present invention also features a method of treating a polymicrobial infection comprising *S. agalactiae* and coagulase-negative *Staphylococcus* (CoNS) (or a method of killing or inhibiting growth of *S. agalactiae* and coagulase-negative *Staphylococcus* (CoNS)), wherein the method comprises introducing levofloxacin to the *S. agalactiae* and CoNS polymicrobial infection (e.g., administering levofloxacin to the patient having or suspected of having a polymicrobial infection with *S. agalactiae* and CoNS), wherein *S. agalactiae* and CoNS together have a decreased odds of resistance to levofloxacin.

The present invention also features a method of treating a polymicrobial infection comprising *S. agalactiae* and coagulase-negative *Staphylococcus* (CoNS) (or a method of killing or inhibiting growth of *S. agalactiae* and coagulase-negative *Staphylococcus* (CoNS)), wherein the method comprises introducing gentamicin to the *S. agalactiae* and CoNS polymicrobial infection (e.g., administering gentamicin to the patient having or suspected of having a polymicrobial infection with *S. agalactiae* and CoNS), wherein *S. agalactiae* and CoNS together have a decreased odds of resistance to gentamicin.

The present invention also features a method of treating a polymicrobial infection comprising *S. agalactiae* and coagulase-negative *Staphylococcus* (CoNS) (or a method of killing or inhibiting growth of *S. agalactiae* and coagulase-negative *Staphylococcus* (CoNS)), wherein the method comprises introducing tetracycline to the *S. agalactiae* and CoNS polymicrobial infection (e.g., administering tetracycline to the patient having or suspected of having a polymicrobial infection with *S. agalactiae* and CoNS), wherein *S. agalactiae* and CoNS together have a decreased odds of resistance to tetracycline.

The present invention also features a method of treating a polymicrobial infection comprising *S. agalactiae* and coagulase-negative *Staphylococcus* (CoNS) (or a method of killing or inhibiting growth of *S. agalactiae* and coagulase-negative *Staphylococcus* (CoNS)), wherein the method comprises introducing TMP/sulfamethoxazole to the *S. agalactiae* and CoNS polymicrobial infection (e.g., administering TMP/sulfamethoxazole to the patient having or suspected of having a polymicrobial infection with *S. agalactiae* and CoNS), wherein *S. agalactiae* and CoNS together have a decreased odds of resistance to TMP/sulfamethoxazole.

The present invention also features a method of treating a polymicrobial infection comprising *S. agalactiae* and coagulase-negative *Staphylococcus* (CONS) (or a method of killing or inhibiting growth of *S. agalactiae* and coagulase-negative *Staphylococcus* (CoNS)), wherein the method comprises introducing vancomycin to the *S. agalactiae* and CoNS polymicrobial infection (e.g., administering vancomycin to the patient having or suspected of having a polymicrobial infection with *S. agalactiae* and CoNS), wherein *S. agalactiae* and CoNS together have a decreased odds of resistance to vancomycin.

Thus, the methods of the present invention also include treating a polymicrobial infection comprising *S. agalactiae* and coagulase-negative *Staphylococcus* (CONS) may comprise introducing (e.g., administering) one or more antimicrobials selected from: ceftriaxone, ciprofloxacin, levofloxacin, gentamicin, tetracycline, TMP/sulfamethoxazole, or vancomycin.

The present invention also features a method of guiding treatment of a polymicrobial infection comprising *S. agalactiae* and coagulase-negative *Staphylococcus* (CONS). The method may comprise detecting the polymicrobial infection with *S. agalactiae* and CoNS and providing a report showing one or more antibiotics to which *S. agalactiae* and CoNS have increased and/or decreases resistance to. The report may help the physician choose an appropriate antibiotic to administer to the patient.

Coagulase-Negative *Staphylococcus* (CONS) and *E. faecalis*

The present invention also features a method of treating a polymicrobial infection comprising *E. faecalis* and coagulase-negative *Staphylococcus* (CONS) (or a method of killing or inhibiting growth of *E. faecalis* and coagulase-negative *Staphylococcus* (CONS)), wherein the method comprises introducing amoxicillin/clavulanate to the *E. faecalis* and CoNS polymicrobial infection (e.g., administering amoxicillin/clavulanate to the patient having or suspected of having a polymicrobial infection with *E. faecalis* and CONS), wherein *E. faecalis* and CoNS together have a decreased odds of resistance to amoxicillin/clavulanate.

The present invention also features a method of treating a polymicrobial infection comprising *E. faecalis* and coagulase-negative *Staphylococcus* (CONS) (or a method of killing or inhibiting growth of *E. faecalis* and coagulase-negative *Staphylococcus* (CoNS)), wherein the method comprises introducing gentamicin to the *E. faecalis* and CoNS polymicrobial infection (e.g., administering gentamicin to the patient having or suspected of having a polymicrobial infection with *E. faecalis* and CoNS), wherein *E. faecalis* and CoNS together have a decreased odds of resistance to gentamicin.

The present invention also features a method of treating a polymicrobial infection comprising *E. faecalis* and coagulase-negative *Staphylococcus* (CONS) (or a method of killing or inhibiting growth of *E. faecalis* and coagulase-negative *Staphylococcus* (CONS)), wherein the method comprises introducing tetracycline to the *E. faecalis* and CoNS polymicrobial infection (e.g., administering tetracycline to the patient having or suspected of having a polymicrobial infection with *E. faecalis* and CoNS), wherein *E. faecalis* and CoNS together have a decreased odds of resistance to tetracycline.

The present invention also features a method of treating a polymicrobial infection comprising *E. faecalis* and coagulase-negative *Staphylococcus* (CONS) (or a method of killing or inhibiting growth of *E. faecalis* and coagulase-negative *Staphylococcus* (CONS)), wherein the method comprises introducing vancomycin to the *E. faecalis* and CoNS polymicrobial infection (e.g., administering vancomycin to the patient having or suspected of having a polymicrobial infection with *E. faecalis* and CoNS), wherein *E. faecalis* and CoNS together have a decreased odds of resistance to vancomycin.

Thus, the methods of the present invention also include treating a polymicrobial infection comprising *E. faecalis* and coagulase-negative *Staphylococcus* (CONS) may comprise introducing (e.g., administering) one or more antimicrobials selected from: amoxicillin/clavulanate, gentamicin, tetracycline, or vancomycin.

The present invention also features a method of guiding treatment of a polymicrobial infection comprising *E. faecalis* and coagulase-negative *Staphylococcus* (CoNS). The method may comprise detecting the polymicrobial infection with *E. faecalis* and CoNS and providing a report showing one or more antibiotics to which *E. faecalis* and CoNS have increased and/or decreases resistance to. The report may help the physician choose an appropriate antibiotic to administer to the patient.

Coagulase-Negative *Staphylococcus* (CONS) and *E. coli*

The present invention also features a method of treating a polymicrobial infection comprising Coagulase-negative *Staphylococcus* (CONS) and *E. coli* (or a method of killing or inhibiting growth of CoNS and *E. coli*), wherein the method comprises introducing amoxicillin/clavulanate to the CoNS and *E. coli* polymicrobial infection (e.g., administering amoxicillin/clavulanate to the patient having or suspected of having a polymicrobial infection with CoNS and *E. coli*), wherein CoNS and *E. coli* together have a decreased odds of resistance to amoxicillin/clavulanate.

The present invention also features a method of treating a polymicrobial infection comprising Coagulase-negative *Staphylococcus* (CONS) and *E. coli* (or a method of killing or inhibiting growth of CoNS and *E. coli*), wherein the method comprises introducing ceftriaxone to the CoNS and *E. coli* polymicrobial infection (e.g., administering ceftriaxone to the patient having or suspected of having a polymicrobial infection with CoNS and *E. coli*), wherein CoNS and *E. coli* together have a decreased odds of resistance to ceftriaxone.

The present invention also features a method of treating a polymicrobial infection comprising Coagulase-negative *Staphylococcus* (CONS) and *E. coli* (or a method of killing or inhibiting growth of CoNS and *E. coli*), wherein the method comprises introducing tetracycline to the CoNS and *E. coli* polymicrobial infection (e.g., administering tetracycline to the patient having or suspected of having a polymicrobial infection with CoNS and *E. coli*), wherein CoNS and *E. coli* together have a decreased odds of resistance to tetracycline.

The present invention also features a method of treating a polymicrobial infection comprising Coagulase-negative *Staphylococcus* (CoNS) and *E. coli* (or a method of killing or inhibiting growth of CoNS and *E. coli*), wherein the method comprises introducing TMP/sulfamethoxazole to the CoNS and *E. coli* polymicrobial infection (e.g., administering TMP/sulfamethoxazole to the patient having or suspected of having a polymicrobial infection with CoNS and *E. coli*), wherein CoNS and *E. coli* together have a decreased odds of resistance to TMP/sulfamethoxazole.

Thus, the methods of the present invention also include treating a polymicrobial infection comprising CoNS and *E. coli* may comprise introducing (e.g., administering) one or more antimicrobials selected from: amoxicillin/clavulanate, ceftriaxone, tetracycline, or TMP/sulfamethoxazole.

The present invention also features a method of guiding treatment of a polymicrobial infection comprising *E. coli* and coagulase-negative *Staphylococcus* (CoNS). The method may comprise detecting the polymicrobial infection with *E. coli* and CoNS and providing a report showing one or more antibiotics to which *E. coli* and CoNS have increased and/or decreases resistance to. The report may help the physician choose an appropriate antibiotic to administer to the patient.

*E. faecalis* and *S. agalactiae*

The present invention also features a method of treating a polymicrobial infection comprising *E. faecalis* and *S. agalactiae* (or a method of killing or inhibiting growth of *E. faecalis* and *S. agalactiae*), wherein the method comprises introducing ampicillin to the *E. faecalis* and *S. agalactiae* polymicrobial infection (e.g., administering ampicillin to the patient having or suspected of having a polymicrobial infection with *E. faecalis* and *S. agalactiae*), wherein *E. faecalis* and *S. agalactiae* together have a decreased odds of resistance to ampicillin.

The present invention also features a method of treating a polymicrobial infection comprising *E. faecalis* and *S. agalactiae* (or a method of killing or inhibiting growth of *E. faecalis* and *S. agalactiae*), wherein the method comprises introducing vancomycin to the *E. faecalis* and *S. agalactiae* polymicrobial infection (e.g., administering vancomycin to the patient having or suspected of having a polymicrobial infection with *E. faecalis* and *S. agalactiae*), wherein *E. faecalis* and *S. agalactiae* together have a decreased odds of resistance to vancomycin.

Thus, the methods of the present invention also include treating a polymicrobial infection comprising *E. faecalis* and *S. agalactiae* may comprise introducing (e.g., administering) one or more antimicrobials selected from: ampicillin or vancomycin.

The present invention also features a method of guiding treatment of a polymicrobial infection comprising *E. faecalis* and *S. agalactiae*. The method may comprise detecting the polymicrobial infection with *E. faecalis* and *S. agalactiae* and providing a report showing one or more antibiotics to which *E. faecalis* and *S. agalactiae* have increased and/or decreases resistance to. The report may help the physician choose an appropriate antibiotic to administer to the patient.

*E. faecalis* and *P. miribilis*

The present invention also features a method of treating a polymicrobial infection comprising *E. faecalis* and *P. miribilis* (or a method of killing or inhibiting growth of *E. faecalis* and *P. miribilis*), wherein the method comprises introducing meropenem to the *E. faecalis* and *P. miribilis* polymicrobial infection (e.g., administering meropenem to the patient having or suspected of having a polymicrobial infection with *E. faecalis* and *P. miribilis*), wherein *E. faecalis* and *P. miribilis* together have a decreased odds of resistance to meropenem.

The present invention also features a method of guiding treatment of a polymicrobial infection comprising *E. faecalis* and *P. miribilis*. The method may comprise detecting the polymicrobial infection with *E. faecalis* and *P. miribilis* and providing a report showing one or more antibiotics to which *E. faecalis* and *P. miribilis* have increased and/or decreases resistance to. The report may help the physician choose an appropriate antibiotic to administer to the patient.

*E. faecalis* and *P. aeruginosa*

The present invention also features a method of treating a polymicrobial infection comprising *E. faecalis* and *P. aeruginosa* (or a method of killing or inhibiting growth of *E. faecalis* and *P. aeruginosa*), wherein the method comprises introducing meropenem to the *E. faecalis* and *P. aeruginosa* polymicrobial infection (e.g., administering meropenem to the patient having or suspected of having a polymicrobial infection with *E. faecalis* and *P. aeruginosa*), wherein *E. faecalis* and *P. aeruginosa* together have a decreased odds of resistance to meropenem.

The present invention also features a method of guiding treatment of a polymicrobial infection comprising *E. faecalis* and *P. aeruginosa*. The method may comprise detecting the polymicrobial infection with *E. faecalis* and *P. aeruginosa* and providing a report showing one or more antibiotics to which *E. faecalis* and *P. aeruginosa* have increased and/or decreases resistance to. The report may help the physician choose an appropriate antibiotic to administer to the patient.

*E. faecalis* and *K. pneumoniae*

The present invention also features a method of treating a polymicrobial infection comprising *E. faecalis* and *K. pneumoniae* (or a method of killing or inhibiting growth of *E. faecalis* and *K. pneumoniae*), wherein the method comprises introducing meropenem to the *E. faecalis* and *K. pneumoniae* polymicrobial infection (e.g., administering meropenem to the patient having or suspected of having a polymicrobial infection with *E. faecalis* and *K. pneumoniae*), wherein *E. faecalis* and *K. pneumoniae* together have a decreased odds of resistance to meropenem.

The present invention also features a method of treating a polymicrobial infection comprising *E. faecalis* and *K. pneumoniae* (or a method of killing or inhibiting growth of *E. faecalis* and *K. pneumoniae*), wherein the method comprises introducing tetracycline to the *E. faecalis* and *K. pneumoniae* polymicrobial infection (e.g., administering tetracycline to the patient having or suspected of having a polymicrobial infection with *E. faecalis* and *K. pneumoniae*), wherein *E. faecalis* and *K. pneumoniae* together have a decreased odds of resistance to tetracycline.

Thus, the methods of the present invention also include treating a polymicrobial infection comprising *E. faecalis* and *K. pneumoniae* may comprise introducing (e.g., administering) one or more antimicrobials selected from: meropenem or tetracycline.

The present invention also features a method of guiding treatment of a polymicrobial infection comprising *E. faecalis* and *K. pneumoniae*. The method may comprise detecting the polymicrobial infection with *E. faecalis* and *K. pneumoniae* and providing a report showing one or more antibiotics to which *E. faecalis* and *K. pneumoniae* have increased and/or decreases resistance to. The report may help the physician choose an appropriate antibiotic to administer to the patient.

*E. faecalis* and *E. coli*

The present invention also features a method of treating a polymicrobial infection comprising *E. faecalis* and *E. coli* (or a method of killing or inhibiting growth of *E. faecalis* and *E. coli*), wherein the method comprises introducing ampicillin/clavulanate to the *E. faecalis* and *E. coli* polymicrobial infection (e.g., administering ampicillin/clavulanate to the patient having or suspected of having a polymicrobial infection with *E. faecalis* and *E. coli*), wherein *E. faecalis* and *E. coli* together have a decreased odds of resistance to ampicillin/clavulanate.

The present invention also features a method of treating a polymicrobial infection comprising *E. faecalis* and *E. coli* (or a method of killing or inhibiting growth of *E. faecalis* and *E. coli*), wherein the method comprises introducing ampicillin/sulbactam to the *E. faecalis* and *E. coli* polymicrobial infection (e.g., administering ampicillin/sulbactam to the patient having or suspected of having a polymicrobial infection with *E. faecalis* and *E. coli*), wherein *E. faecalis* and *E. coli* together have a decreased odds of resistance to ampicillin/sulbactam.

The present invention also features a method of treating a polymicrobial infection comprising *E. faecalis* and *E. coli* (or a method of killing or inhibiting growth of *E. faecalis* and *E. coli*), wherein the method comprises introducing levofloxacin to the *E. faecalis* and *E. coli* polymicrobial infection (e.g., administering levofloxacin to the patient having or suspected of having a polymicrobial infection with *E. faecalis* and *E. coli*), wherein *E. faecalis* and *E. coli* together have a decreased odds of resistance to levofloxacin.

The present invention also features a method of treating a polymicrobial infection comprising *E. faecalis* and *E. coli* (or a method of killing or inhibiting growth of *E. faecalis* and *E. coli*), wherein the method comprises introducing meropenem to the *E. faecalis* and *E. coli* polymicrobial infection (e.g., administering meropenem to the patient having or suspected of having a polymicrobial infection with *E. faecalis* and *E. coli*), wherein *E. faecalis* and *E. coli* together have a decreased odds of resistance to meropenem.

The present invention also features a method of treating a polymicrobial infection comprising *E. faecalis* and *E. coli* (or a method of killing or inhibiting growth of *E. faecalis* and *E. coli*), wherein the method comprises introducing tetracycline to the *E. faecalis* and *E. coli* polymicrobial infection (e.g., administering tetracycline to the patient having or suspected of having a polymicrobial infection with *E. faecalis* and *E. coli*), wherein *E. faecalis* and *E. coli* together have a decreased odds of resistance to tetracycline.

Thus, the methods of the present invention also include treating a polymicrobial infection comprising *E. faecalis* and *E. coli* may comprise introducing (e.g., administering) one or more antimicrobials selected from: ampicillin/clavulanate, ampicillin/sulbactam, levofloxacin, meropenem, or tetracycline.

The present invention also features a method of guiding treatment of a polymicrobial infection comprising *E. faecalis* and *E. coli*. The method may comprise detecting the polymicrobial infection with *E. faecalis* and *E. coli* and providing a report showing one or more antibiotics to which *E. faecalis* and *E. coli* have increased and/or decreases resistance to. The report may help the physician choose an appropriate antibiotic to administer to the patient.

*E. coli* and *S. agalactiae*

The present invention also features a method of treating a polymicrobial infection comprising *E. coli* and *S. agalactiae* (or a method of killing or inhibiting growth of *E. coli* and *S. agalactiae*), wherein the method comprises introducing ampicillin to the *E. coli* and *S. agalactiae* polymicrobial infection (e.g., administering ampicillin to the patient having or suspected of having a polymicrobial infection with *E. coli* and *S. agalactiae*), wherein *E. coli* and *S. agalactiae* together have a decreased odds of resistance to ampicillin.

The present invention also features a method of treating a polymicrobial infection comprising *E. coli* and *S. agalactiae* (or a method of killing or inhibiting growth of *E. coli* and *S. agalactiae*), wherein the method comprises introducing cefepime to the *E. coli* and *S. agalactiae* polymicrobial infection (e.g., administering cefepime to the patient having or suspected of having a polymicrobial infection with *E. coli* and *S. agalactiae*), wherein *E. coli* and *S. agalactiae* together have a decreased odds of resistance to cefepime.

The present invention also features a method of treating a polymicrobial infection comprising *E. coli* and *S. agalactiae* (or a method of killing or inhibiting growth of *E. coli* and *S. agalactiae*), wherein the method comprises introducing ceftazidime to the *E. coli* and *S. agalactiae* polymicrobial infection (e.g., administering ceftazidime to the patient having or suspected of having a polymicrobial infection with *E. coli* and *S. agalactiae*), wherein *E. coli* and *S. agalactiae* together have a decreased odds of resistance to ceftazidime.

The present invention also features a method of treating a polymicrobial infection comprising *E. coli* and *S. agalactiae* (or a method of killing or inhibiting growth of *E. coli* and *S. agalactiae*), wherein the method comprises introducing ceftriaxone to the *E. coli* and *S. agalactiae* polymicrobial infection (e.g., administering ceftriaxone to the patient having or suspected of having a polymicrobial infection with *E. coli* and *S. agalactiae*), wherein *E. coli* and *S. agalactiae* together have a decreased odds of resistance to ceftriaxone.

The present invention also features a method of treating a polymicrobial infection comprising *E. coli* and *S. agalactiae* (or a method of killing or inhibiting growth of *E. coli* and *S. agalactiae*), wherein the method comprises introducing ciprofloxacin to the *E. coli* and *S. agalactiae* polymicrobial infection (e.g., administering ciprofloxacin to the patient having or suspected of having a polymicrobial infection with *E. coli* and *S. agalactiae*), wherein *E. coli* and *S. agalactiae* together have a decreased odds of resistance to ciprofloxacin.

The present invention also features a method of treating a polymicrobial infection comprising *E. coli* and *S. agalactiae* (or a method of killing or inhibiting growth of *E. coli* and *S. agalactiae*), wherein the method comprises introducing levofloxacin to the *E. coli* and *S. agalactiae* polymicrobial infection (e.g., administering levofloxacin to the patient having or suspected of having a polymicrobial infection with *E. coli* and *S. agalactiae*), wherein *E. coli* and *S. agalactiae* together have a decreased odds of resistance to levofloxacin.

The present invention also features a method of treating a polymicrobial infection comprising *E. coli* and *S. agalactiae* (or a method of killing or inhibiting growth of *E. coli* and *S. agalactiae*), wherein the method comprises introducing tetracycline to the *E. coli* and *S. agalactiae* polymicrobial infection (e.g., administering tetracycline to the patient having or suspected of having a polymicrobial infection with *E. coli* and *S. agalactiae*), wherein *E. coli* and *S. agalactiae* together have a decreased odds of resistance to tetracycline.

The present invention also features a method of treating a polymicrobial infection comprising *E. coli* and *S. agalactiae* (or a method of killing or inhibiting growth of *E. coli* and *S. agalactiae*), wherein the method comprises introducing TMP/sulfamethoxazole to the *E. coli* and *S. agalactiae* polymicrobial infection (e.g., administering TMP/sulfamethoxazole to the patient having or suspected of having a polymicrobial infection with *E. coli* and *S. agalactiae*), wherein *E. coli* and *S. agalactiae* together have a decreased odds of resistance to TMP/sulfamethoxazole.

Thus, the methods of the present invention also include treating a polymicrobial infection comprising *E. coli* and *S. agalactiae* may comprise introducing (e.g., administering) one or more antimicrobials selected from: ampicillin, cefepime, ceftazidime, ceftriaxone, ciprofloxacin, levofloxacin, tetracycline, or TMP/sulfamethoxazole.

The present invention also features a method of guiding treatment of a polymicrobial infection comprising *E. coli* and *S. agalactiae*. The method may comprise detecting the polymicrobial infection with *E. coli* and *S. agalactiae* and providing a report showing one or more antibiotics to which *E. coli* and *S. agalactiae* have increased and/or decreases resistance to. The report may help the physician choose an appropriate antibiotic to administer to the patient.

*E. coli* and *P. mirabilis*

The present invention also features a method of treating a polymicrobial infection comprising *E. coli* and *P. mirabilis* (or a method of killing or inhibiting growth of *E. coli* and *P.*

*mirabilis*), wherein the method comprises introducing cefaclor to the *E. coli* and *P. mirabilis* polymicrobial infection (e.g., administering cefaclor to the patient having or suspected of having a polymicrobial infection with *E. coli* and *P. mirabilis*), wherein *E. coli* and *P. mirabilis* together have a decreased odds of resistance to cefaclor.

The present invention also features a method of treating a polymicrobial infection comprising *E. coli* and *P. mirabilis* (or a method of killing or inhibiting growth of *E. coli* and *P. mirabilis*), wherein the method comprises introducing cefazolin to the *E. coli* and *P. mirabilis* polymicrobial infection (e.g., administering cefazolin to the patient having or suspected of having a polymicrobial infection with *E. coli* and *P. mirabilis*), wherein *E. coli* and *P. mirabilis* together have a decreased odds of resistance to cefazolin.

The present invention also features a method of treating a polymicrobial infection comprising *E. coli* and *P. mirabilis* (or a method of killing or inhibiting growth of *E. coli* and *P. mirabilis*), wherein the method comprises introducing cefoxitin to the *E. coli* and *P. mirabilis* polymicrobial infection (e.g., administering cefoxitin to the patient having or suspected of having a polymicrobial infection with *E. coli* and *P. mirabilis*), wherein *E. coli* and *P. mirabilis* together have a decreased odds of resistance to cefoxitin.

The present invention also features a method of treating a polymicrobial infection comprising *E. coli* and *P. mirabilis* (or a method of killing or inhibiting growth of *E. coli* and *P. mirabilis*), wherein the method comprises introducing ceftazidime to the *E. coli* and *P. mirabilis* polymicrobial infection (e.g., administering ceftazidime to the patient having or suspected of having a polymicrobial infection with *E. coli* and *P. mirabilis*), wherein *E. coli* and *P. mirabilis* together have a decreased odds of resistance to ceftazidime.

The present invention also features a method of treating a polymicrobial infection comprising *E. coli* and *P. mirabilis* (or a method of killing or inhibiting growth of *E. coli* and *P. mirabilis*), wherein the method comprises introducing ceftriaxone to the *E. coli* and *P. mirabilis* polymicrobial infection (e.g., administering ceftriaxone to the patient having or suspected of having a polymicrobial infection with *E. coli* and *P. mirabilis*), wherein *E. coli* and *P. mirabilis* together have a decreased odds of resistance to ceftriaxone.

Thus, the methods of the present invention also include treating a polymicrobial infection comprising *E. coli* and *P. mirabilis* may comprise introducing (e.g., administering) one or more antimicrobials selected from: cefaclor, cefazolin, cefoxitin, ceftazidime, or ceftriaxone.

The present invention also features a method of guiding treatment of a polymicrobial infection comprising *E. coli* and *P. mirabilis*. The method may comprise detecting the polymicrobial infection with *E. coli* and *P. mirabilis* and providing a report showing one or more antibiotics to which *E. coli* and *P. mirabilis* have increased and/or decreases resistance to. The report may help the physician choose an appropriate antibiotic to administer to the patient.

*E. coli* and *K. pneumoniae*

The present invention also features a method of treating a polymicrobial infection comprising *E. coli* and *K. pneumoniae* (or a method of killing or inhibiting growth of *E. coli* and *K. pneumoniae*), wherein the method comprises introducing levofloxacin to the *E. coli* and *K. pneumoniae* polymicrobial infection (e.g., administering levofloxacin to the patient having or suspected of having a polymicrobial infection with *E. coli* and *K. pneumoniae*), wherein *E. coli* and *K. pneumoniae* together have a decreased odds of resistance to levofloxacin.

The present invention also features a method of treating a polymicrobial infection comprising *E. coli* and *K. pneumoniae* (or a method of killing or inhibiting growth of *E. coli* and *K. pneumoniae*), wherein the method comprises introducing tetracycline to the *E. coli* and *K. pneumoniae* polymicrobial infection (e.g., administering tetracycline to the patient having or suspected of having a polymicrobial infection with *E. coli* and *K. pneumoniae*), wherein *E. coli* and *K. pneumoniae* together have a decreased odds of resistance to tetracycline.

Thus, the methods of the present invention also include treating a polymicrobial infection comprising *E. coli* and *K. pneumoniae* may comprise introducing (e.g., administering) one or more antimicrobials selected from: levofloxacin or tetracycline.

The present invention also features a method of guiding treatment of a polymicrobial infection comprising *E. coli* and *K. pneumoniae*. The method may comprise detecting the polymicrobial infection with *E. coli* and *K. pneumoniae* and providing a report showing one or more antibiotics to which *E. coli* and *K. pneumoniae* have increased and/or decreases resistance to. The report may help the physician choose an appropriate antibiotic to administer to the patient.

*E. coli* and *K. oxytoca*

The present invention also features a method of treating a polymicrobial infection comprising *E. coli* and *K. oxytoca* (or a method of killing or inhibiting growth of *E. coli* and *K. oxytoca*), wherein the method comprises introducing cefepime to the *E. coli* and *K. oxytoca* polymicrobial infection (e.g., administering cefepime to the patient having or suspected of having a polymicrobial infection with *E. coli* and *K. oxytoca*), wherein *E. coli* and *K. oxytoca* together have a decreased odds of resistance to cefepime.

The present invention also features a method of treating a polymicrobial infection comprising *E. coli* and *K. oxytoca* (or a method of killing or inhibiting growth of *E. coli* and *K. oxytoca*), wherein the method comprises introducing ciprofloxacin to the *E. coli* and *K. oxytoca* polymicrobial infection (e.g., administering ciprofloxacin to the patient having or suspected of having a polymicrobial infection with *E. coli* and *K. oxytoca*), wherein *E. coli* and *K. oxytoca* together have a decreased odds of resistance to ciprofloxacin.

The present invention also features a method of treating a polymicrobial infection comprising *E. coli* and *K. oxytoca* (or a method of killing or inhibiting growth of *E. coli* and *K. oxytoca*), wherein the method comprises introducing tetracycline to the *E. coli* and *K. oxytoca* polymicrobial infection (e.g., administering tetracycline to the patient having or suspected of having a polymicrobial infection with *E. coli* and *K. oxytoca*), wherein *E. coli* and *K. oxytoca* together have a decreased odds of resistance to tetracycline.

Thus, the methods of the present invention also include treating a polymicrobial infection comprising *E. coli* and *K. oxytoca* may comprise introducing (e.g., administering) one or more antimicrobials selected from: cefepime, ciprofloxacin, or tetracycline.

The present invention also features a method of guiding treatment of a polymicrobial infection comprising *E. coli* and *K. oxytoca*. The method may comprise detecting the polymicrobial infection with *E. coli* and *K. oxytoca* and providing a report showing one or more antibiotics to which *E. coli* and *K. oxytoca* have increased and/or decreases resistance to. The report may help the physician choose an appropriate antibiotic to administer to the patient.

The present invention also features methods for treating a patient having or suspected of having a polymicrobial infection comprising a combination of *E. coli* and *K. Pneumo-* niae. In certain embodiments, the method comprising: detecting the presence of both *E. coli* and *K. Pneumoniae* in a source of the infection obtained from the patient; and administering to the patient an antibiotic other than ampicillin/sulbactam or cefaclor, wherein *E. coli* and *K. Pneumoniae* together have an increased odds of resistance to ampicillin/sulbactam and cefaclor.

The present invention also features methods for treating a patient having or suspected of having a polymicrobial infection comprising a combination of *E. faecalis* and *K. Pneumoniae*. In certain embodiments, the method comprises detecting the presence of both *E. faecalis* and *K. Pneumoniae* in a source of the infection obtained from the patient; and administering to the patient an antibiotic other than amoxicillin/clavulanate or ampicillin/sulbactam, wherein *E. faecalis* and *K. Pneumoniae* together have an increased odds of resistance to amoxicillin/clavulanate and ampicillin/sulbactam.

The present invention also features methods for treating a patient having or suspected of having a polymicrobial infection comprising a combination of *E. faecalis* and *S. agalactiae*. In certain embodiments, the method comprises detecting the presence of both *E. faecalis* and *S. agalactiae* in a source of the infection obtained from the patient; and administering to the patient an antibiotic other than tetracycline wherein *E. faecalis* and *S. agalactiae* together have an increased odds of resistance to tetracycline.

The present invention also features methods for treating a patient having or suspected of having a polymicrobial infection comprising a combination of *E. coli* and CoNS. In certain embodiments, the method comprises detecting the presence of both *E. coli* and CoNS in a source of the infection obtained from the patient; and administering to the patient an antibiotic other than levofloxacin, wherein *E. coli* and CoNS together have an increased odds of resistance to levofloxacin.

The present invention is not limited to the aforementioned polymicrobial infections and administered antibiotics.

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description and claims.

BRIEF DESCRIPTION OF THE SEVERAL VIEWS OF THE DRAWING(S)

The patent application or application file contains at least one drawing executed in color. Copies of this patent or patent application publication with color drawing(s) will be provided by the Office upon request and payment of the necessary fee.

The features and advantages of the present invention will become apparent from a consideration of the following detailed description presented in connection with the accompanying drawings in which:

FIG. 1 shows the effects of *E. coli* and *K. pneumoniae* interactions on resistance to ampicillin/sulbactam, cefaclor, and tetracycline.

FIG. 2 shows the effects of organism interactions on antibiotic resistance. An upward arrow indicates an increase in resistance. A downward arrow indicates a decrease in resistance (an increase in susceptibility).

FIG. 3 depicts examples of polymicrobial infections that experience decreases or increases in antibiotic sensitivity, relative to monomicrobial infections.

FIG. 4 is a continuation of FIG. 3, depicting examples of polymicrobial infections that experience decreases or increases in antibiotic sensitivity, relative to monomicrobial infections.

FIG. 5 depicts various odds ratios of resistance, comparing polymicrobial infections with monomicrobial infections.

FIG. 6 depicts examples of polymicrobial infections that experience decreases or increases in antibiotic sensitivity, relative to monomicrobial infections.

FIG. 7 is a continuation of FIG. 6, depicting examples of polymicrobial infections that experience decreases or increases in antibiotic sensitivity, relative to monomicrobial infections.

FIG. 8 is a continuation of FIG. 6 and FIG. 7, depicting examples of polymicrobial infections that experience decreases or increases in antibiotic sensitivity, relative to monomicrobial infections.

Figure 10:
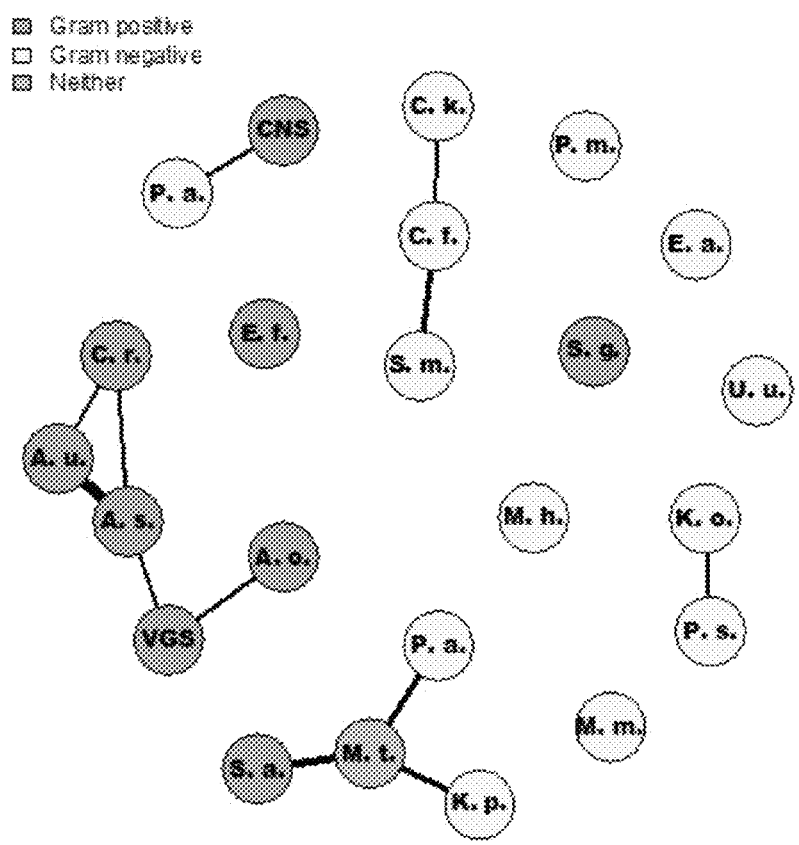

FIG. 10 shows correlations between organisms found in polymicrobial infections, excluding *E. coli*. The strength of correlation is represented by the width of the edge connecting the genes. Only correlations greater than 0.1 are shown.

FIG. 11 depicts an exemplary Antibiotic Source Plate with well contents and antibiotic concentration (μg/mL). Nitro=nitrofurantoin, Cipro=ciprofloxacin, Mero=meropenem, Ceftiaxone=ceftriaxone, TMP/SMX=trimethoprim+sulfamethoxazole, Pip/Tazo=piperacillin+tazobactam, Levo=levofloxacin, Cefoxitin=cefoxitin, Tetra=tetracycline, Amp/Sulb=ampicillin+sulbactam, Amp=ampicillin, and Vanco=vancomycin.

FIG. 12 depicts an exemplary Antibiotic Source Plate with well contents and antibiotic concentration (μg/mL). Cefazolin=cefazolin, Cefepime=cefepime, Ceftazidime=ceftazidime, Gentamicin=gentamicin, Amox/Clav=amoxicillin+clavulanate, Cefaclor=cefaclor.

TERMS

As used herein, the term "Highest Single Agent Interaction Principle" refers to a statistical model wherein the resistance of the polymicrobial infection is predicted to be the resistance of the bacteria with the highest resistance. For example, if species A is resistant with a probability 20%, and species B is resistant with a probability 50%, then the probability of resistance of the pool is 50%.

As used herein, the term "Union Principle" refers to a statistical model wherein the polymicrobial infection of species A and B is made up of one colony (or one genetic variant) of species A and one colony (or one genetic variant) of species B, and the polymicrobial infection is resistant if either the colony of species A is resistant, or if the colony of species B is resistant. For example, if an antibiotic is applied to the polymicrobial infection, it may kill off species A, but if species B survives, the polymicrobial infection is called resistant. For example, if species A is resistant with a probability 20%, and species B is resistant with a probability 50%, then the probability of resistance of the pool is:

$$P(\text{pool resistance}) = P(A) + P(B) - P(A \text{ and } B)$$

As used herein, the term "Logistic Additive Model" refers to a statistical model wherein the effects of species A and species B on the resistance of the polymicrobial infection is estimated in a logistic model. The effect of species A is the odds ratio of resistance when species A is present relative to when it is not present; similarly, the effect of species B is the odds ratio of resistance when species B is present relative to when it is not. The additive model predicts the effect of both species as the sum of the log odds-ratio; or the product of the two individual odds-ratios. For example, if the background resistance rate is 50%, the expected polymicrobial infection (species A and B) resistance with no interactions is 20%; if the background resistance rate is 20%, the expected polymicrobial infection resistance is 50%.

DETAILED DESCRIPTION OF THE INVENTION

Antibiotics

The present methods are conducted using a plurality of antibiotics selected from the large number available to treat patients. Antibiotics (also referred to as anti-microbial agents or anti-bacterial agents) include, but are not limited to, penicillins, tetracyclines, cephalosporins, quninolones, lincomycins, macrolides, sulronamides, glycopeptide antibiotics, aminoglycosides, carbapenems, ansamycins, lipopeptides, monobactams, nitrofurans, oxaxolidinones, and polypeptides.

Penicillin antibiotics include, but are not limited to, penicillin, methicillin, amoxicillin, ampicillin, flucloxacillin, penicillin G, penicillin V, carbenicillin, piperacillin, ticarcillin, oxacillin, dicloxacillin, azlocillin, cloxacillin, mezlocillin, temocillin, and nafcillin. Additionally, penicillin antibiotics are often used in combination with beta-lactamase inhibitors to provide broader spectrum activity; these combination antibiotics include amoxicillin/clavulanate, ampicillin/sulbactam, piperacillin/tazobactam, and clavulanate/ticarcillin.

Tetracycline antibiotics include, but are not limited to, tetracycline, doxycycline, demeclocycline, minocycline, and oxytetracycline.

Cephalosporin antibiotics include, but are not limited to, cefadroxil, cephradine, cefazolin, cephalexin, cefepime, ceftaroline, loracarbef, cefotetan, cefuroxime, cefprozil, cefoxitin, cefaclor, ceftibuten, cetriaxone, cefotaxime, cefpodoxime, cefdinir, cefixime, cefditoren, ceftizoxime, cefoperazone, cefalotin, cefamanadole, ceftaroline fosamil, cetobiprole, and ceftazidime. Cephalosporin antibiotics are often used in combination with beta-lactamase inhibitors to provide broader spectrum activity; these combination antibiotics include, but are not limited to, avibactam/ceftazidime and ceftolozane/tazobactam.

Quinolone antibiotics include, but are not limited to, lomefloxacin, ofloxacin, norfloxacin, gatifloxacin, ciprofloxacin, moxifloxacin, levofloxacin, gemifloxacin, cinoxacin, nalidixic acid, trovaloxacin, enoxacin, grepafloxacin, temafloxacin, and sparfloxacin.

Lincomycin antibiotics include, but are not limited to, clindamycin and lincomycin.

Macrolide antibiotics include, but are not limited to, azithromycin, clarithromycin, erythromycin, telithromycin, dirithromycin, roxithromycin, troleandomycin, spiramycin, and fidazomycin.

Sulfonamide antibiotics include, but are not limited to, sulfamethoxazole, sulfasalazine, mafenide, sulfacetamide, sulfadiazine, silver sufadiazine, sulfadimethoxine, sulfanilimide, sulfisoxazole, sulfonamidochrysoidine, and sulfisoxazole. Sulfonamide antibiotics are often used in combination with trimethoprim to improve bactericidal activity.

Glycopeptide antibiotics include, but are not limited to, dalbavancin, oritavancin, telavancin, teicoplanin, and vancomycin.

Aminoglycoside antibiotics include, but are not limited to, paromomycin, tobramycin, gentamicin, amikacin, kanamycin, neomycin, netilmicin, streptomycin, and spectinomycin.

Carbapenem antibiotics include, but are not limited to, imipenem, meropenem, doripenem, ertapenem, and imipenem/cilastatin.

Ansamycin antibiotics include, but are not limited to, geldanamycin, herbimycin, and rifaximin.

Lipopeptide antibiotics include, but are not limited to, daptomycin.

Monobactam antibiotics include, but are not limited to, aztreonam.

Nitrofuran antibiotics include, but are not limited to furazolidone and nitrofurantoin.

Oxaxolidinone antibiotics include, but are not limited to, linezolid, posizolid, radezolid, and torezolid.

Polypeptide antibiotics include, but are not limited to, bacitracin, colistin, and polymyxin B.

Other antibiotics which are not part of any of the above-mentioned groups include, but are not limited to, clofazimine, dapsone, capreomycin, cycloserine, ethambutol, ethionamide, isoniazid, pyrazinamide, rifampicin, rifabutin, rifapentine, streptomycin, arsphenamide, chloramphenicol, fosfomycin, fusidic acid, metronidazole, mupirocin, platensimycin, quinupristin/dalfopristin, thiamphenicol, tigecycline, tinidazole, and trimethoprim.

Additionally, the scope of the presently disclosed methods encompasses the inclusion of antibiotics not yet known, or not yet approved by regulatory authorities. The presently claimed assay can be performed with any anti-bacterial agent and is not limited to the antibiotics disclosed herein.

Treatment of Polymicrobial Infections

Disclosed herein are methods for detecting polymicrobial infections as well as treating polymicrobial infections, wherein a mixed population of microbes (e.g., bacteria) are present in a patient sample and the microbes are not first isolated from the sample.

For example, the present invention describes specific polymicrobial infections and methods of treating said infections, wherein a particular antibiotic or a group of antibiotics are selected based on the composition of the polymicrobial infections. As is described below, certain polymicrobial infections show a surprising reduction in antibiotic resistance relative to what might be expected. For example, *Klebsiella* has a relatively high resistance rate to ampicillin. However, it was surprisingly found that *Klebsiella* combined with coagulase-negative *Staphylococcus* (CNS or CoNS) have a reduced resistance to ampicillin relative to what might be expected (e.g., based on the union principle or single highest agent principle).

Figure 1:
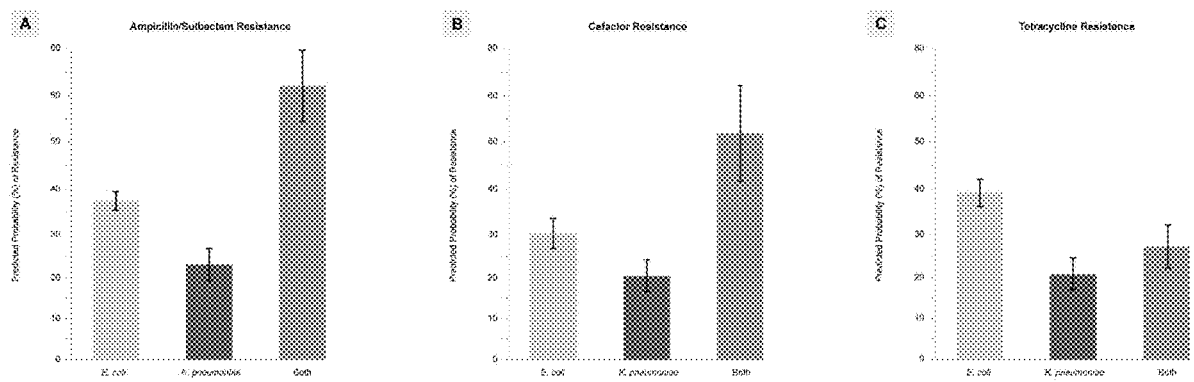

FIG. 1 shows a detailed example of the combinations of *E. coli* and *K. pneumoniae* and the effects on resistance to ampicillin/sulbactam, cefaclor, and tetracycline. When combined, *E. coli* and *K. pneumoniae* have a higher resistance to ampicillin/sulbactam and cefaclor relative to what would be expected (e.g., based on the union principle or single highest agent principle). However, *E. coli* and *K. pneumoniae* together have a reduced resistance to tetracycline relative to what would be expected (e.g., based on the union principle or single highest agent principle).

Figure 2:
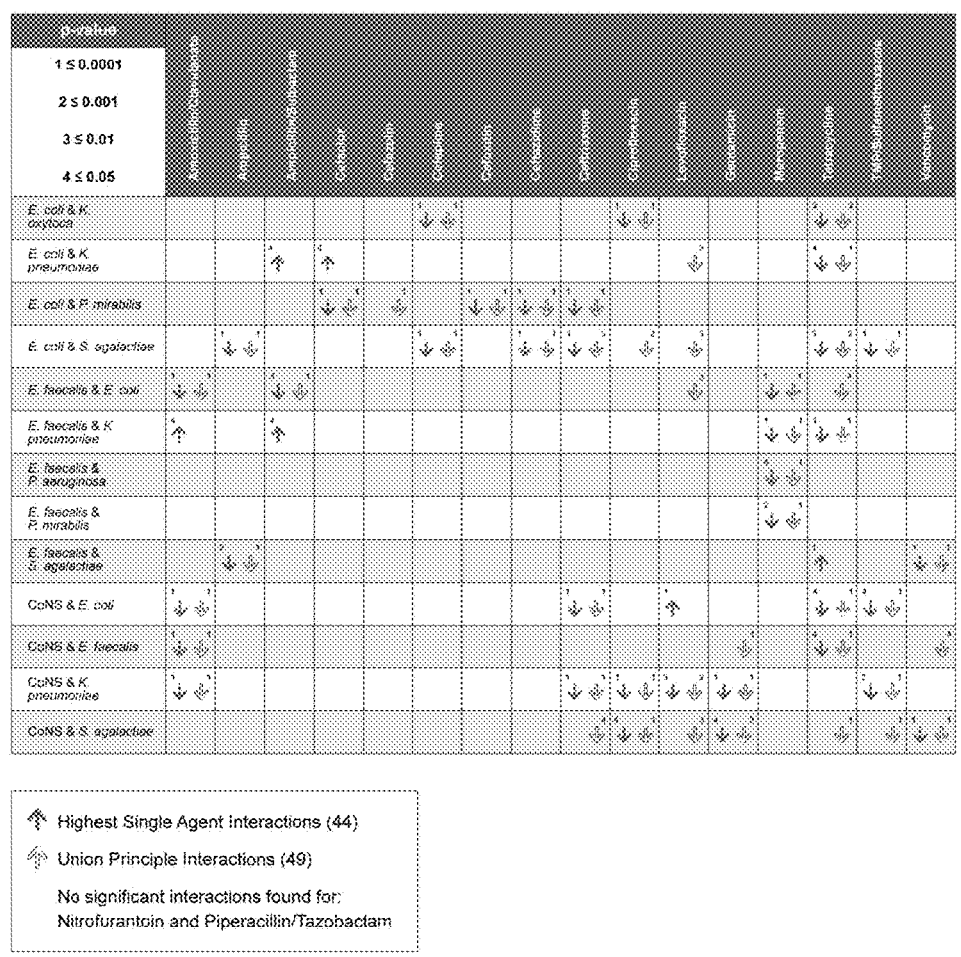

FIG. 2 shows the effects of organism interactions on antibiotic resistance for a variety of microbes and antibiotics. An upward arrow indicates an increase in resistance (e.g., a decrease in susceptibility). A downward arrow indicates a decrease in resistance (e.g., an increase in susceptibility). Examples of organism interactions that result in a decrease in resistance (e.g., increase in susceptibly) includes but is not limited to:

Coagulase-negative *Staphylococcus* (CONS) and *E. coli*, or coagulase-negative *Staphylococcus* (CONS) and *E. faecalis*, or coagulase-negative *Staphylococcus* (CONS) and *K. pneumoniae*, or *E. faecalis* and *E. coli* show a decrease in resistance to amoxicilliniclavulanate. *E. coli* and *S. agalactiae*, or *E. faecalis* and *S. agalactiae* show a decrease in resistance to ampicillin. *E. faecalis* and *E. coli* show a decrease in resistance to ampicillin/sulbactam. *E. coli* and *P. mirabilis* show a decrease in resistance to cefaclor or cefazolin. *E. coli* and *K. oxytoca*, or *E. coli* and *S. agalactiae* show a decrease in resistance to cefepime. *E. coli* and *P. mirabilis* show a decrease in resistance to cefoxitin. *E. coli* and *P. mirabilis*, or *E. coli* and *S. agalactiae* show a decrease in resistance to ceftazidime.

Coagulase-negative *Staphylococcus* (CoNS) and *E. coli*, or Coagulase-negative *Staphylococcus* (CONS) and *K. pneumoniae*, or Coagulase-negative *Staphylococcus* (CoNS) and *S. agalactiae*, or *E. coli* and *P. mirabilis*, or *E. coli* and *S. agalactiae* show a decrease in resistance to ceftriaxone.

Coagulase-negative *Staphylococcus* (CONS) and *K. pneumoniae*, or Coagulase-negative *Staphylococcus* (CoNS) and *S. agalactiae*, or *E. coli* and *K. oxytoca*, or *E. coli* and *S. agalactiae* show a decrease in resistance to ciprofloxacin.

Coagulase-negative *Staphylococcus* (CoNS) and *E. coli*, or Coagulase-negative *Staphylococcus* (CoNS) and *K. pneumoniae*, or Coagulase-negative *Staphylococcus* (CoNS) and *S. agalactiae*, or *E. coli* and *S. agalactiae*, or *E. faecalis* and *K. pneumoniae* show a decrease in resistance to levofloxacin.

Coagulase-negative *Staphylococcus* (CoNS) and *E. faecalis*, or Coagulase-negative *Staphylococcus* (CoNS) and *K. pneumoniae*, or Coagulase-negative *Staphylococcus* (CoNS) and *S. agalactiae* show a decrease in resistance to gentamicin.

*E. faecalis* and *E. coli*, or *E. faecalis* and *K. pneumoniae*, or *E. faecalis* and *P. aeruginosa*, or *E. faecalis* and *P. mirabilis* show a decrease in resistance to meropenem. Coagulase-negative *Staphylococcus* (CoNS) and *E. coli*, or Coagulase-negative *Staphylococcus* (CoNS) and *E. faecalis*, or Coagulase-negative *Staphylococcus* (CoNS) and *S. agalactiae*, or *E. coli* and *K. oxytoca*, or *E. coli* and *K. pneumoniae*, or *E. coli* and *S. agalactiae*, or *E. faecalis* and *E. coli*, or *E. faecalis* and *K. pneumoniae* show a decrease in resistance to tetracycline. Coagulase-negative *Staphylococcus* (CoNS) and *E. coli*, or Coagulase-negative *Staphylococcus* (CoNS) and *K. pneumoniae*, or Coagulase-negative *Staphylococcus* (CONS) and *S. agalactiae*, or *E. faecalis* and *E. coli* show a decrease in resistance to TMP/sulfamethoxazole. Coagulase-negative *Staphylococcus* (CONS) and *E. faecalis*, or Coagulase-negative *Staphylococcus* (CONS) and *S. agalactiae*, or *E. faecalis* and *S. agalactiae* show a decrease in resistance to vancomycin.

Figure 9:
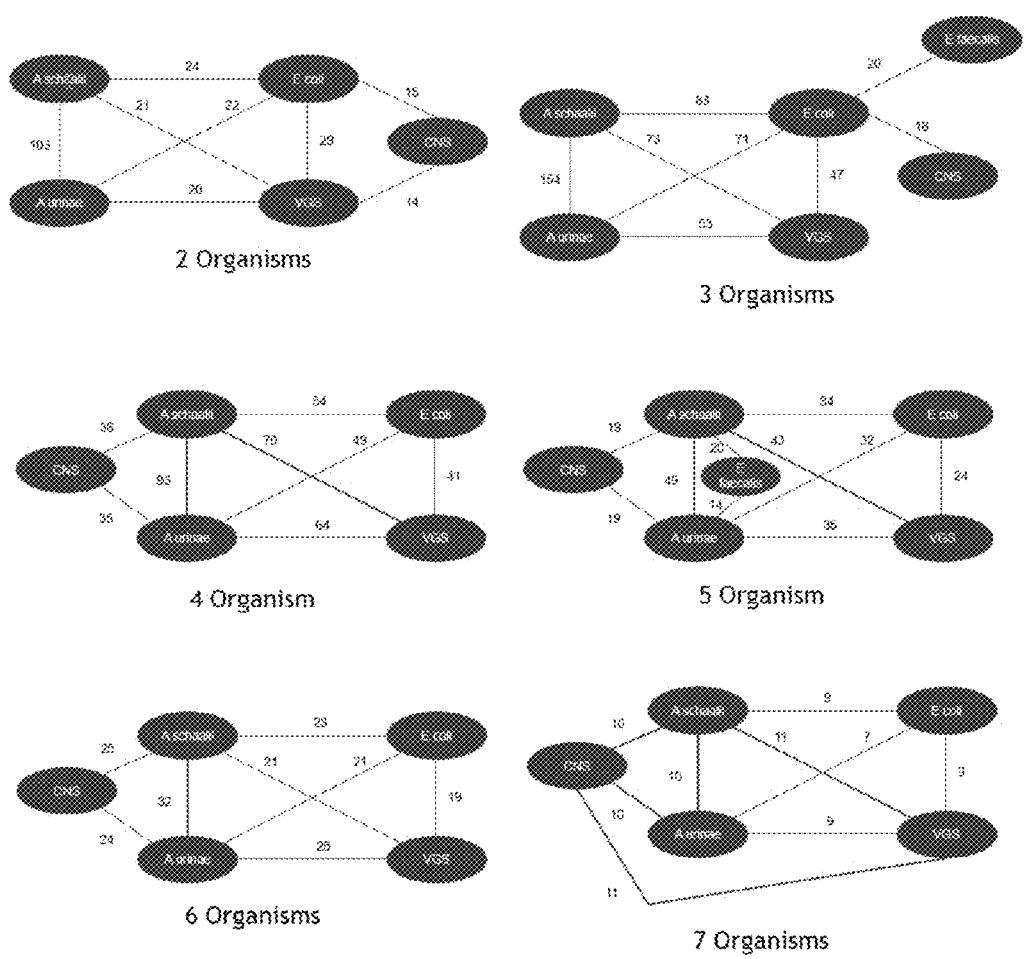
FIG. 9 shows correlations between organisms found in polymicrobial infections, particularly polymicrobial infections with 2, 3, 4, 5, 6, or 7 organisms.

FIG. 3, FIG. 4, FIG. 5, FIG. 6, FIG. 7, and FIG. 8 also show effects of organism interactions on antibiotic resistance. FIG. 9 and FIG. 10 show correlations between the presence of particular organisms found in polymicrobial infections.

Thus, the present invention describes methods of treating polymicrobial infections, such as the aforementioned polymicrobial infections, with appropriate antibiotics, such as the antibiotics to which the polymicrobial infections have decreased resistance. The methods herein may comprise the detection of the presence of the combination of the bacteria (e.g., the two or more bacteria in a polymicrobial infection) in a source of the infection obtained from the patient. The detection process may not necessarily involve first isolating each bacterium from the source of infection.

For example, the present invention features methods of treating a patient having or suspected of having a polymicrobial infection comprising a combination of *E. faecalis* and *E. coli*. In certain embodiments, the method comprises administering one or a combination of amoxicillin/clavulanate, ampicillin/sulbactam, levofloxacin, meropenem, or tetracycline.

The present invention also features methods for treating a patient having or suspected of having a polymicrobial infection comprising a combination of *E. faecalis* and *K. pneumoniae*. In certain embodiments, the method comprises administering one or a combination of meropenem or tetracycline.

The present invention also features methods for treating a patient having or suspected of having a polymicrobial infection comprising a combination of *E. faecalis* and *P. aeruginosa*. In certain embodiments, the method comprises administering meropenem to the patient.

The present invention also features methods for treating a patient having or suspected of having a polymicrobial infection comprising a combination of *E. faecalis* and *P. miribilis*. In certain embodiments, the method comprises administering meropenem to the patient.

The present invention also features methods for treating a patient having or suspected of having a polymicrobial infection comprising a combination of *E. faecalis* and *S. agalactiae*. In certain embodiments, the method comprises administering one or a combination of ampicillin or vancomycin.

The present invention is not limited to the aforementioned examples and encompasses any example described herein, including the figures.

Antibiotic Resistance (ABR) Testing Plates

Referring to other disclosed methods herein, samples may be collected from subjects according to standard collection protocols in sterile containers and are transported to the testing facility.

An example of the preparation of the antibiotic resistance (ABR) testing plates involves two steps. First is preparation of antibiotic solutions and the second is preparation of the bacterial growth medium plate. The antibiotics to be tested for any given sample include antibiotics known to be useful for treating the tissue having the suspected infection, or any antibiotics requested by a medical or laboratory professional having knowledge of the particular patient sample. It is anticipated that most assays will be performed with a standard panel of antibiotics based on the type and location of infection suspected by a medical professional. In some embodiments, the standard panel of antibiotics comprises nitrofurantoin, ciprofloxacin, meropenem, ceftriaxone, trimethoprim/sulfamethoxazole, piperacillin/tazobactam, levofloxacin, cefoxitin, tetracycline, ampicillin/sulbactam, ampicillin, and vancomycin. However, patients with known antibiotic allergies or sensitivities, or with a history of antibiotic resistance, may require customized panels of antibiotics. The assay can be performed simultaneous with an unlimited number of antibiotics.

Antibiotic stock solutions are prepared using solvents suitable for each antibiotic and then 10× solutions are prepared and stored in multi-well plates to allow efficient transfer to testing plates. Each antibiotic is tested at a minimum of concentrations. In some embodiments, three concentrations, four concentrations, five concentrations, six concentrations, seven concentrations, eight concentrations, nine concentrations, or ten concentrations of an antibiotic, or antibiotic combination, are included in the assay. Typically serial dilutions of the antibiotics are prepared wherein each dilution represents half the concentration of the higher concentration. The 10× antibiotic solutions are stored in the multi-well plate according to a plate plan established for the antibiotic panel chosen for the assay. Exemplary plate plans are depicted in the Antibiotic Source Plates in FIG. 11 and FIG. 12. Antibiotic stocks and 10× solutions are stored at 2-8° C. until needed.

The ABR testing plates may be multi-well plates (e.g., 6-well, 12-well, 24-well, 48-well, 96-well, 384-well plates, or any multi-well plate suitable for this purpose) capable of containing bacterial growth medium and culturing bacteria. In some embodiments, the plates are 96-well plates. In some embodiments, sterile agar-bacterial growth medium is dispensed into each well of the plate. Exemplary agar-bacterial growth medium include, but are not limited to Mueller-Hinton agar, blood agar, trypticase soy agar, etc. After the agar has solidified at room temperature, 1/10 volume (of bacterial growth medium) of 10× antibiotic solution is added to each well of the test plate according to the pre-determined plate plan. After the antibiotics have been introduced to the bacterial growth medium, the plates are allowed to rest for at least one hour. For long-term storage, the antibiotic-containing ABR plates are stored at 2-8° C. In some embodiments, sterile liquid broth bacterial growth medium mixed with sample is dispensed into each well of the plate containing 1/10 volume (of bacterial growth medium) of 10× antibiotic solution arrayed according to a pre-determined plate plan. Multi-well plates containing 1/10 volume (of final well volume of bacterial growth medium and antibiotic solution) are stored at 2-8° C. for later use or long-term storage.

Samples for the disclosed antibiotic resistance testing may be optionally diluted in sterile aqueous solution or mixed with bacterial growth medium. In some embodiments, a volume of sample for the disclosed antibiotic resistance testing are first mixed with a growth medium and incubated for 0-24 hours at an incubation temperature of 35±4° C. The samples are then diluted with saline and then mixed with growth medium and added to room temperature ABR testing plates at 9/10 volume of each well in the multi-well plate. In some embodiments, samples are added to room temperature ABR plates at 1/20 volume of bacterial growth medium present in the well. A single patient specimen is used for each ABR plate. If multiple patient specimens are to be tested, each specimen is assayed in its own plate. Once inoculated, the plates are covered and incubated to encourage bacterial growth. Embodiments where a single sample is assayed using more than one plate are also within the scope of the present method.

The plates can be used to culture either anaerobic or aerobic bacteria. For culture of anaerobic bacteria, the plates are incubated at a temperature and in a reduced-oxygen environment to encourage growth of anaerobic bacteria. For culture of aerobic bacteria, the plates are incubated at a temperature and in an oxygen-containing environment to encourage growth of aerobic bacteria.

The incubation temperature can vary depending on the expected types of bacteria but will most likely be in a range of 35-40° C. The plates containing samples are incubated for 12-48 hours, 12-24 hours, 24-28 hours, 12-36 hours, 14-30 hours, 16-24 hours, 16-20 hours, or 16-18 hours, or any range bounded by these numbers.

In some embodiments, wherein the assay is performed with an agar-containing medium, after incubation, bacteria present in each well are recovered by resuspension in an aqueous liquid. Suitable liquids include, but are not limited to, water, saline, culture medium, etc. The aqueous liquid should be sterile, or at least free from bacterial growth. A volume of liquid equal to 100% of the volume of bacterial growth medium is carefully added to the wells of the ABR plate and allowed to sit for at least 30 minutes. In some embodiments, the plates are allowed to sit for 35 minutes, 40 minutes, 45 minutes, 50 minutes, or 60 minutes. The resulting suspension is then carefully removed from each well into individual wells of a clean multi-well plate according to the predetermined plate plan. The plates are optionally agitated to cause mixing of the bacteria with the liquid prior to removal of the suspension. In some embodiments wherein the assay is performed using liquid growth medium, the multi-well plate will be applied to $OD_{600}$ measurement immediately after incubation.

The multi-well plate containing the bacteria-containing suspension is then read in a spectrophotometer. The optical density of the recovered liquid is measured at $OD_{600}$ multiple times to correct for uneven distribution of bacteria particles in the suspension. In some embodiments, the plates are read one time, two times, three times, four times, five times, six times, seven times, or eight times. The multiple plate reads occur in sequence without allowing the suspension to settle in the wells.

The multiple $OD_{600}$ of each well are averaged to provide an accurate quantitation of bacteria present in each well under the specific conditions. Each well's average $OD_{600}$ is then adjusted for background by subtracting the average $OD_{600}$ measurements of a well where no bacteria could grow to yield a blanked value. In some embodiments, this no-growth well contains a blend of antibiotics (AB-blend). In some embodiments, this no-growth well contains sodium azide (Na-Azide). The blanked value is representative of the ability of bacteria to grow in the presence of the particular antibiotic in the well.

The blanked results are then converted into a "resistance" (R) or "sensitive" (S) score based on a threshold value. $OD_{600}$ measurements greater than or equal to the threshold are interpreted as resistant, while measurements below the threshold are interpreted as sensitive.

In some embodiments, the threshold value is for an agar-containing medium. In some embodiments, a threshold value has been determined at 0.010 to 1.000, 0.010-0.090, 0.015 to 0.035, or 0.020 to 0.030 based on correlations to a standard reference method. In some embodiments, the threshold value as been determined at about 0.010, about 0.015, about 0.020, about 0.025, about 0.030, about 0.035, about 0.040, about 0.045, about 0.050, about 0.055, about 0.060, about 0.065, about 0.070, about 0.075, about 0.080, about 0.085, or about 0.090 based on correlations to a standard reference method. In some embodiments, a threshold value has been determined at 0.025 based on correlations to a standard reference method.

In some embodiments, the threshold value is for a liquid medium. In some embodiments, a threshold value has been determined at 0.010-1.000, 0.020-0.090, 0.050-0.080, 0.055 to 0.075, or 0.060 to 0.070 based on correlation to a consensus score between two standard reference methods. In some embodiments, the threshold value as been determined at about 0.010, about 0.015, about 0.020, about 0.025, about 0.030, about 0.035, about 0.040, about 0.045, about 0.050, about 0.055, about 0.060, about 0.065, about 0.070, about 0.075, about 0.080, about 0.085, about 0.090, or about 0.095 based on correlation to a consensus score between two standard reference methods. In some embodiments, a threshold value has been determined at 0.065 based on correlation to a consensus score between two standard reference methods.

In other embodiments, any adjusted $OD_{600}$ measurement greater than blank $OD_{600}$ measurement can be determined as indicative of bacterial growth and applied as a threshold value by correlation to a standard reference method or combination of reference methods.

Minimal inhibitory concentrations for each effective antibiotic are then calculated based on the sensitivity or resistance of the culture at the multiple antibiotic concentrations.

Results of the antibiotic resistance assay disclosed herein are transmitted to the appropriate medical professional who then has the option of prescribing an antibiotic, or antibiotics, shown to be active against the patient's infection, changing the antibiotic to a more effective antibiotic, or ordering additional testing.

EXAMPLES

The following are non-limiting examples of the present invention. It is to be understood that said examples are not intended to limit the present invention in any way. Equivalents or substitutes are within the scope of the present invention.

Example 1. Bacterial Organism Interactions as Detected by Pooled Antibiotic Susceptibility Testing (P-AST) in Polymicrobial Urine Specimens The standard of care for the diagnosis of UTI is a standard urine culture and sensitivity testing (SUC), and has served to guide treatment since the early 1950's. The methodology relies on an "*Escherichia coli* (*E. coli*) centric" view of infections that suggested that UTI's are caused by a single or perhaps two pathogens. Recent findings have underscored not only are the vast majority of uropathogens missed by routine culture but that up to 39% of these infections are polymicrobial in nature. In conjunction, antibiotic resistance has been well-studied in monomicrobial infections, but has been less well characterized in polymicrobial infections in the clinical setting. Yet, interactions between organisms can alter responses to antibiotics.

Currently, antibiotic susceptibility testing (AST) ignores bacterial interactions. In AST, each bacterium is tested in isolation against an antibiotic, providing no opportunity to assess bacterial interactions. Ignoring bacterial interactions can either lead to potential treatment failure or prevent the use of efficacious antibiotics. Both scenarios can have serious clinical consequences. Pooled Antibiotic Susceptibly Testing (P-AST), on the other hand, permits the ability to consider interactions since the assay involves simultaneously growing the detected organisms together in the presence of antibiotics and then measures susceptibility. P-AST may therefore provide therapeutic options that take into consideration the ability of organisms to respond to antibiotics in conjunction with bacterial interactions.

The present invention describes Pooled Antibiotic Susceptibility Testing (P-AST), which involves simultaneously growing all detected bacteria together in the presence of antibiotics and then measuring susceptibility. Thus, P-AST considers interactions between cohabiting bacterial species. Urine specimens were obtained from patients presenting with UTI-like symptoms to 37 urology clinics. The odds of resistance were estimated for 18 antibiotics relative to increasing numbers of bacterial species in a specimen. It was found that antimicrobial susceptibility patterns in polymicrobial specimens differed from those observed in monomicrobial specimens. Since standard of care relies on assessment of antibiotic susceptibility in monomicrobial infections, these findings show that P-AST could serve as a more accurate predictor of antibiotic susceptibility.

The following study combines data from two studies of antibiotic resistance patterns in elderly patients presenting with symptoms consistent with a UTI. Retrospective data and patient information were obtained from a single site for 613 patients. Prospective data and patient information were obtained for 2,511 patients who presented at any of 37 geographically disparate clinics in the United States. All subjects met the following inclusion and exclusion criteria. Inclusion criteria included: symptoms of acute cystitis, complicated UTI, persistent UTI, recurrent UTI, prostatitis, pyelonephritis, interstitial cystitis (at any age), symptoms of other conditions at years of age, specimen volumes sufficient to permit urine culture and Multiplex Polymerase Chain Reaction (M-PCR) combined with Pooled Antibiotic Sensitivity Testing (P-AST), patient informed consented, documented times at which the specimens were collected and stabilized with boric acid in grey-top tubes. Exclusion criteria included prior participation in this study, antibiotics taken for any reason other than UTI at the time of enrollment, chronic (≥10 days) indwelling catheters, self-catheterization, and urinary diversion. Antibiotic susceptibility data were available for 1,352 of the 3,124 patients (43.3%).

DNA extraction was performed using the KingFisher/MagMAX™ Automated DNA Extraction instrument and the MagMAX™ DNA Multi-Sample Ultra Kit (ThermoFisher, Carlsbad, Calif.). 1 mL of urine were transferred to 96-well deep-well plates, sealed, and centrifuged to concentrate the samples, and then the supernatant was removed. Enzyme Lysis Mix (200 μL/well) was added to the samples, which were then incubated for 20 min at 65° C. Proteinase K Mix (PK Mix) was added (50 μL/well) and incubated for 30 min at 65° C. Lysis buffer (125 μL/well) and DNA Binding Bead Mix (40 μL/well) were added, and the samples were vortexed for a minimum of 5 min. Each 96-well plate was loaded into the KingFisher/MagMAX Automated DNA Extraction instrument, which was operated in accordance with standard operating procedures.

DNA analysis was conducted using the Guidance® UTI Test (Pathnostics, Irvine, Calif.), which consists of both M-PCR and P-AST. Samples were mixed with universal PCR master mix and amplified using TaqMan technology on the Life Technologies 12K Flex OpenArray System™ (Life Technologies, Carlsbad, Calif.). DNA samples were spotted in duplicate on 112-format OpenArray chips. Plasmids unique to each bacterial species being tested were used as positive controls. Any appropriate target may be usable as an inhibition control, e.g., *Candida tropicalis, B. atrophaeus*, etc. A data analysis tool developed by Pathnostics was used to sort data, assess the quality of data, summarize control sample data, identify positive assays, calculate concentrations, and generate draft reports. Probes and primers were used to detect the following pathogenic bacteria: *Acinetobacter baumannii, Actinotignum schaalii, Aerococcus urinae, Alloscardovia omnicolens, Citrobacter freundii, Citrobacter koseri, Corynebacterium riegelii, Enterobacter aerogenes, Enterococcus faecalis, Escherichia coli, Klebsiella oxytoca, Klebsiella pneumoniae, Morganella morganii, Mycobacterium tuberculosis, Mycoplasma genita-*

*lium, Mycoplasma hominis, Pantoea agglomerans, Proteus mirabilis, Providencia stuartii, Pseudomonas aeruginosa, Serratia marcescens, Staphylococcus aureus, Streptococcus agalactiae*, and *Ureaplasma urealyticum*. Probes and primers also were used to detect the following bacterial groups: Coagulase negative staphylococci (CONS) (*Staphylococcus epidermidis, Staphylococcus haemolyticus, Staphylococcus lugdunensis, Staphylococcus saprophyticus*); Viridans group streptococci (VGS) (*Streptococcus anginosus, Streptococcus oralis, Streptococcus pasteuranus*).

The Pooled Antibiotic Sensitivity Test (P-AST) is permitting the organisms identified to grow in the presence of antibiotics and measuring the minimum concentration of antibiotic to inhibit growth. Antibiotic susceptibility testing is performed when at least a single organism within a pool of organisms reaches a certain threshold, (e.g., at least 3,000 cells/ml, at least 5,000 cells/ml, at least 10,000 cells/ml, etc.) and can grow in the presence of the antibiotic in the assay within the time of testing. (Note: 10,000 cells/ml is equivalent to 10,000 CFU/ml.) The present invention is not limited to a 10,000 cells/mL threshold. These pools of organism(s) are inoculated into growth medium then placed onto an antibiotic laden "spec plate" that is then incubated and analyzed for growth. The breakpoints are derived from the CLSI breakpoints.

P-AST was performed by aliquoting 1 mL of patient urine specimen into a 1.7 mL microcentrifuge tube. After centrifugation, the supernatant was aspirated and discarded, leaving approximately 100 or 50 µL (minimum volume left above pellet created from centrifugation) of patient sample in the microcentrifuge tube. One mL of Mueller Hinton Growth Media was then aliquoted into the patient sample in the microcentrifuge tube and the tubes were incubated at 35° C. in a non-$CO_2$ incubator for 6 hours. Non-inoculated liquid MH-media is incubated as the negative control to confirm the media used is not contaminated. Those samples that reached a minimum threshold of 10,000 cells/mL were then diluted by aliquoting 0.5 mL of sample into a 50 mL conical tube containing Mueller Hinton Growth Media (in this example, the dilution was 1:60, e.g., 500 µL was added to 29.5 mL). 96-well plates pre-loaded with antibiotics were then inoculated with diluted samples and incubated along with control plates for 12-16 hours at 35° C. in a single layer. Optical density of samples was then read on a DensiCHEK plate reader. The DensiCHEK instrument is used to measure the concentration of turbid samples considered positive because PCR-ID result was >=10,000 cells/mL. The turbid samples were diluted/normalized to the same concentration and then added to a volume of liquid, e.g., 29.5 mL of liquid MH-media. A spectrophotometer (plate reader) is used to measure optical density of the samples in wells of antibiotics and inoculum in order to determine if there is growth in a well. The present invention is not limited to a concentration of 10,000 cells/mL.

Logistic regression was used to compare resistance rates in monomicrobial and polymicrobial infections. Specifically, 18 different logistic regression models were fit to the data: the response variable was an indicator of whether the specimen was resistant to the specific antibiotic or not and the predictor variable was an indicator of whether the infection was monomicrobial or polymicrobial. Specimens were classified as monomicrobial if a single bacterial species was detected above the 10000 cells/mL threshold; they were classified as polymicrobial if two or more distinct bacteria species were detected above that threshold. Similar logistic regression models also were run, using the number of distinct bacterial species as the predictor variable. The present invention is not limited to a concentration of 10,000 cells/mL.

Interactions between pairs of bacterial species were investigated using a logistic regression model to predict resistance in the presence of specific bacterial species. Bacterial species that tested positive in at least 30 samples were considered in the regression model: these 16 species were *A. schaalii, A. urinae, A. omnicolens*, CoNS, *C. riegelii, E. faecalis, E. coli, K. oxytoca, K. pneumoniae, M. morganii, P. mirabilis, P. aeruginosa, S. aureus, S. agalactiae, U. urealyticum*, VGS. Backward stepwise model selection was performed on the model with all main effects and all pairwise interactions using an enter significance level of $\alpha=0.10$ and an exit significance level of $\alpha=0.05$ to obtain the best fitting model. This model was used to predict resistance rates when a specific organism was present or when a specific pair of organisms were present.

Using the logistic regression model described above, the resistance rate for a pair of species was compared to the resistance rates for each species alone. Two different principles were applied to calculate the expected resistance rate to a pair of species that do not interact: (a) Highest Single Agent Principle (HSAP) (a commonly used model for drug interactions) and (b) Union Principle (UP) (also used to model drug interactions).

Using the HSAP, a pair of organisms was considered to have an interaction if the resistance rate of the pair of organisms was statistically different from the highest resistance rate of each of the two organisms. This principle is based on the idea that a pool of two organisms will survive application of a specific antibiotic only if the more resistant bacteria survives. When antibiotic is applied to the pool, it may kill off species A, but if species B survives, the pool is called resistant.

The UP assumes a pair of bacteria (species A and B) is made up of one genetic variant of species A and one genetic variant of species B, and that the pool is resistant if either species A is resistant or if species B is resistant. If species A is resistant with probability P(A), and species B is resistant with probability P(B), then the probability of resistance of the pool is:

$$P(\text{pool resistance})=P(A)+P(B)-P(A)P(B)$$

This assumes the two species do not interact, and therefore act independently. Interactions were statistically tested using bootstrapped samples of the 3,124 patients: each patient was randomly selected with replacement. A logistic regression with terms in the best fitting model selected as above was fit to each bootstrapped sample. The predicted resistance when the pair of organisms was present was compared to the predicted resistance to each organism alone using the model fit to the bootstrap sample and either the HSAP or UP. 5,000 bootstrapped samples were generated and analyzed. If 97.5% or greater of the bootstrapped samples demonstrated a pool resistance higher than expected, the interaction was deemed to show a statistically significant interaction with increased resistance. If 97.5% or greater of the bootstrapped samples demonstrated a pool resistance lower than expected, the interaction was deemed to show a statistically significant interaction with decreased resistance.

A total of 3,124 patients, from two studies and from 37 geographically disparate urology clinics in the United States, presenting with symptoms consistent with a UTI, were initially included in the study. P-AST data were available for 43.3% (1352) of these patients. Their mean age was 75 years. Sixty-six percent (887/1,352) were female, whereas 34% (465/1,352) male.

By M-PCR, 38.9% (1,214/3,124) of the specimens were negative for bacteria, whereas 61.1% (1910/3124) were positive. P-AST data were available for 1,352 (70.7%) of these 1,910 positive specimens. Of these 1,352 specimens, 43.9% (594/1352) were monomicrobial, whereas 56.1% (758/1352) were polymicrobial.

Five hundred and fifty eight positive samples lacked antimicrobial susceptibility data for the following reasons: (1) no species were detected at ≥10,000 cells/mL (correlating to colony forming units/mL) and thus no species were tested against antibiotics; (2) the species detected by PCR were fastidious (i.e., they required specific growth conditions, extremely restrictive growth conditions, or extreme length of time in order to perform susceptibility testing); (3) prior antimicrobial use caused bacteria to fail to thrive in the P-AST assay; or (4) species were not identified because the M-PCR reaction was inhibited (based upon comparison to negative and positive controls). M-PCR inhibition can occur when an interfering substance prevents the amplification and subsequent detection of the PCR product associated with targeted DNA. The present invention is not limited to a concentration of 10,000 cells/mL.

Odds ratios of antibiotic resistance in polymicrobial versus monomicrobial specimens are shown in Table 1, along with the odds ratio of resistance for each increase in the number of bacterial species in polymicrobial specimens. The resistance rates of polymicrobial samples were generally higher than the rates of monomicrobial samples: 10 of 18 antibiotics had statistically higher resistance rates for polymicrobial samples. The odds of resistance for each additional species identified in a polymicrobial specimen increased for ampicillin, amoxicillin/clavulanate, five of the six of the cephalosporins tested, vancomycin, and tetracycline. The opposite was true for piperacillin/tazobactam, where each additional species in a polymicrobial specimen resulted in a 75% decrease in the odds of resistance (95% CI 0.61, 0.94, p=0.01). The present invention is not limited to a concentration of 10,000 cells/mL.

Referring to Table 1, the numbers in parentheses are 95% confidence interval boundaries. Column 2 represents odds ratios of resistance for polymicrobial versus monomicrobial specimens. Column 4 presents odds ratios of resistance for each additional bacterial species in a specimen. (*Significant p-value.)

TABLE 1

| Antibiotic | Odds Ratio of Resistance Polymicrobial v. Monomicrobial | p-value | Odds Ratio of Resistance for Each Additional Species | p-value |
|---|---|---|---|---|
| Penicillins | | | | |
| Ampicillin | 1.37 (1.10, 1.70) | 0.005* | 1.14 (1.05, 1.24) | 0.001* |
| Combinations | | | | |
| Amoxicillin/Clavulanate | 1.38 (1.09, 1.74) | 0.008* | 1.16 (1.07, 1.26) | 0.0005* |
| Ampicillin/Sulbactam | 1.13 (0.89, 1.42) | 0.32 | 1.05 (0.96, 1.14) | 0.30 |
| Trimethoprim/Sulfamethoxazole | 1.09 (0.88, 1.37) | 0.43 | 0.98 (0.91, 1.07) | 0.69 |
| Piperacillin/Tazobactam | 0.69 (0.43, 1.11) | 0.12 | 0.75 (0.61, 0.94) | 0.010* |
| Cephalosporins | | | | |
| Cefaclor | 1.42 (1.15, 1.77) | 0.001* | 1.15 (1.06, 1.25) | 0.0006* |
| Cefazolin | 1.38 (1.11, 1.72) | 0.004* | 1.15 (1.07, 1.25) | 0.0004* |
| Cefepime | 1.45 (1.16, 1.80) | 0.001* | 1.12 (1.03, 1.21) | 0.006* |
| Cefoxitin | 1.41 (1.14, 1.76) | 0.002* | 1.10 (1.01, 1.19) | 0.020* |
| Ceftazidime | 1.31 (1.05, 1.62) | 0.02* | 1.07 (0.99, 1.15) | 0.10 |
| Ceftriaxone | 1.25 (1.01, 1.56) | 0.04* | 1.09 (1.01, 1.18) | 0.03* |
| Carbapenams | | | | |
| Meropenem | 1.28 (0.99, 1.65) | 0.06 | 1.08 (0.99, 1.18) | 0.10 |
| Aminoglycosides | | | | |
| Gentamicin | 1.17 (0.90, 1.51) | 0.23 | 1.01 (0.92, 1.11) | 0.78 |
| Fluroroqinolones | | | | |
| Ciprofloxacin | 1.20 (0.96, 1.51) | 0.11 | 1.03 (0.95, 1.12) | 0.45 |
| Levofloxacin | 1.20 (0.95, 1.53) | 0.13 | 1.05 (0.97, 1.14) | 0.25 |
| Nitrofurans | | | | |
| Nitrofurantoin | 1.03 (0.64, 1.65) | 0.9 | 0.90 (0.74, 1.08) | 0.25 |
| Tetracyclines | | | | |
| Tetracyclines | 1.26 (1.02, 1.57) | 0.04* | 1.11 (1.02, 1.20) | 0.010* |
| Glycopeptides | | | | |
| Vancomycin | 2.15 (1.63, 2.84) | <0.0001 | 1.38 (1.21, 1.56) | <0.0001 |

FIG. 2 shows the effect of specific species interactions on the probability of increased or decreased resistance to each antibiotic tested. No interactions were detected for nitrofurantoin and piperacillin/tazobactam. Whereas the odds of resistance to ampicillin, amoxicillin/clavulanate, 6 different cephalosporins, vancomycin, and tetracycline increased with increasing number of detected species (FIG. 2), there were 19 instances for which 11 of the 13 bacterial pairs resulted in reduced susceptibility to the same antibiotics.

Using HSAP, there were 44 instances for which 13 pairs of bacteria showed statistically significant interactions that either increased or decreased the probability of resistance to the antibiotics tested. According to the HSAP principle, most interactions resulted in a decreased probability of resistance. Only 6/44 (13.6%) pairings resulted in increased odds of antibiotic resistance, whereas a decreased probability occurred in 38/44 (86.4%) of pairings.

The bacterial combinations that increased the probability of antibiotic resistance according to the HSAP model were *E. faecalis* and *K. pneumoniae* (amoxicillin/clavulanate, p=0.02 and ampicillin/sulbactam, p=0.03), *E. coli* and *K. pneumoniae* (ampicillin/sulbactam, p=0.04 and cefaclor, p=0.05), CoNS and *E. coli* and (levofloxacin, p<0.001), *E. faecalis* and *S. agalactiae* (tetracycline, p<0.001).

The UP model identified 49 statistically significant interactions, all of which showed decreased probability of resistance to the antibiotics tested.

To illustrate the model, one specific pair is presented in graphical form. FIG. 1 shows the predicted probabilities of resistance to ampicillin/sulbactam, cefaclor, and tetracycline by monomicrobial positive cultures for *E. coli* and *K. pneumoniae* and a polymicrobial culture positive for both *E. coli* and *K. pneumoniae*. When the HSAP model was used, the pairing of *E. coli* and *K. pneumoniae* resulted in either a significant increase or significant decrease in the probability of resistance depending on the antibiotic tested. For example, when ampicillin/sulbactam or cefaclor was applied to the combination of *E. coli* and *K. pneumoniae*, the resistance rate was higher than either *E. coli* or *K. pneumoniae* alone. In contrast, the resistance rate to tetracycline of same combination of species, *E. coli* and *K. pneumoniae*, was intermediate between the resistance rates to each species alone.

These results demonstrate that polymicrobial infections, which constituted 56.1% (758/1,352) of positive samples with susceptibility results, can alter response to antibiotics. They also show that the alteration is sensitive to both the specific bacterial combination and the antibiotic tested. Thirteen bacterial pairs had one or more significant interactions when tested on 16 of the 18 antibiotics using HSAP and UP. Of these interactions, 38 resulted in a decreased probability of resistance, while 6 resulted in an increased probability of resistance. The combination of *E. coli* and *K. pneumoniae* resulted in an increased probability of resistance to ampicillin/sulbactam and cefaclor, but decreased probability of resistance to tetracycline. *E. faecalis* together with *K. pneumoniae* resulted in increased resistance to amoxicillin/clavulanate and ampicillin/sulbactam, but decreased resistance to levofloxacin, meropenem, and tetracycline. *E. faecalis* combined with *S. agalactiae* produced an increase in resistance to tetracycline, but decreased resistance to ampicillin and vancomycin. Similarly, the combination of CoNS and *E. coli* produced an increased probability in resistance to levofloxacin, but the same combination produced a decreased probability in resistance to amoxicillin/clavulanate, ceftriaxone, tetracycline, and trimethoprim/sulfamethoxazole. These differences may be attributed to the unique mechanisms of action of the specific antibiotics.

A similar set of contrasts is observed from the perspective of individual antibiotics. Different pairs of bacteria caused both increased and decreased resistance to amoxicillin/clavulanate, ampicillin/sulbactam, cefaclor, levofloxacin, and tetracycline. For instance, *E. coli* combined with *K. pneumoniae* produced an increase in resistance to cefaclor, while *E. coli* combined with *P. mirabilis* produced a decrease in resistance to cefaclor. These results highlight the importance of accurate identification of bacteria in polymicrobial infections: a difference in identification of one species can influence antibiotic resistance.

The observed effects on antibiotic resistance in polymicrobial infections may be due to cooperative and/or competitive interactions between bacteria. Resistant bacteria can cooperatively protect susceptible bacteria by degrading antibiotics, as occurs when secreted beta-lactamase degrades beta-lactam antibiotics. Antibiotic resistance can be conferred by one bacterium on another bacterium by means of horizontal gene transfer (HGT) of antibiotic resistance genes. Bacterial interactions with host macrophages can promote HGT. For instance, *P. aeruginosa*, when present in biofilms, produces extracellular DNA that induces neutrophils to produce pro-inflammatory cytokines (IL-8 and IL-1 beta). The ensuing inflammation can promote HGT involving *E. coli*. Interestingly, some antibiotics can also promote HGT: antibiotics that cause bacterial lysis release DNA and proteins that can be taken up by other bacteria. In addition, one bacterium can stimulate gene expression in another bacterium, resulting in upregulation of efflux pumps leading to increased antibiotic resistance. Bacterial community spatial structuring within a polymicrobial biofilm may also affect the efficacy of antibiotics.

Decreased resistance to antibiotics in polymicrobial specimens may also be due to competitive mechanisms between bacteria. *P. aeruginosa* has been documented to produce antibiotics, whereas *Enterococcus* species produce and secrete bacteriocins. Gram-negative bacteria have developed a number of specialized secretion systems that can perform protective functions. Type V secretion systems secrete proteases that digest IgA, surface receptors that bind the constant region of IgG, and virulence factor/adhesin proteins that promote colonization. Type VI secretion systems allow Gram-negative bacteria to secrete antibacterial toxins directly into other bacteria. At the same time, Type VI systems mediate DNA acquisition via HGT; an example is the capacity for *A. baumannii* to rapidly acquire resistance genes from *E. coli* by means of Type VI transfer systems.

One type of bacterial interaction can cause a paradoxical result: cross-feeding between bacteria can produce decreased antibiotic resistance. This may explain our observed decreased probability of antibiotic resistance seen in most specific organism combinations. Cross-feeding is a process by which one organism produces metabolites that promote the survival of another organism. However, this interaction can produce a chain of dependencies, leaving the entire chain only as resistant as the most susceptible bacterium. Adamowicz et al. showed that bacterial species were inhibited at significantly lower antibiotic concentrations in cross-feeding communities than in monoculture; coined as the "weakest link" model.

Example 2. Antibiotic Resistance (ABR) Assay Utilizing Agar-Containing Medium

Urine samples suitable for processing with this assay are collected, transported, and stored using BD Vacutainer (gray top) tubes or other suitable leak-proof sterile container. Urine samples may be held at room temperature for 48 hours before test results are compromised.

Antibiotics not received in ready-made solutions were dissolved in appropriate solvent and according to their individual solubility at 10× the concentration desired in the assay as antibiotic stocks. Antibiotic stocks are stored at 2-8° C. and protected from direct sunlight. Prepared antibiotic stock solutions were aliquoted into a 96-deep well plate (Thermo Fisher Scientific) to form an Antibiotic Source Plate, as shown in FIG. 11 and identified by antibiotic name and concentration (μg/mL; 10× final concentration). Antibiotics include in this assay were nitrofurantoin, ciprofloxacin, meropenem, ceftriaxone, trimethoprim, sulfamethoxazole; piperacillin, tazobactam, levofloxacin, cefoxitin, tetracycline, ampicillin, sulbactam, and vancomycin, either singly or in combination. One well was designated AB-blend which contained a combination of antibiotics to ensure there was no bacterial growth.

One hundred microliters of Mueller-Hinton agar medium was aliquoted into each appropriate well position of a 96-well microplate (VIS 96/F-PS, Eppendorf). The medium was allowed to solidify at room temperature for at least 10 min.

The antibiotics (10 μL) at various concentrations were then aliquoted into desired wells from the Antibiotic Source Plate. After the antibiotics were introduced to the agar medium, the ABR microplates were allowed to sit for at least 1 hr before use. If long-term storage is required, ABR microplates containing antibiotic-infuse agar are stored at 2-8° C. in the dark.

At the time of testing, urine samples were diluted 1:20 in sterile saline and vortexed. Each patient sample utilized a single ABR microplate. Five microliters of diluted patient sample were added to each well of the room temperature microplate, the plate was sealed and incubated for 16-18 hr at 37° C.

After incubation, the plate was removed from the incubator and carefully uncovered. Two-hundred microliters of deionized water were added to each well to suspend cells present above the agar and the plates incubated at room temperature for 30 min. After 30 min, 100 μl from each well was removed to a new plate and the $OD_{600}$ was determined in a spectrophotometer. Five separate reads were taken of each plate and a mean $OD_{600}$ measurement calculated.

Controls include: No-antibiotic control, Negative control plate, and AB-Blend. No antibiotic control: Any well containing medium that is not infused with antibiotics to ensure viability of bacterial cells present in patient urine samples and included in each plate. If the no-antibiotic control for any given patient does not yield growth, a secondary test is performed using the same patient sample without dilution. Negative control plate: Microplate containing antibiotic-infused agar medium without addition of patient sample or cultured bacterial organisms to ensure non-contamination of reagents. AB-Blend: One or more wells containing a combination of antibiotics to ensure there is no bacterial growth.

Raw data collected from the plate is depicted in Table 2. Data in spreadsheet form was arranged as "Well Position" adjacent to its corresponding "Mean" OD.

TABLE 2

| Well | Mean |
| --- | --- |
| A7 | 0.6960 |
| A8 | 0.0388 |
| A9 | 0.0744 |
| A10 | 0.0385 |
| A11 | 0.0477 |
| A12 | 0.4550 |
| B7 | 0.0387 |
| B8 | 0.0390 |
| B9 | 0.0412 |
| B10 | 0.4250 |
| B11 | 0.0449 |
| B12 | 0.4880 |

TABLE 2-continued

| Well | Mean |
| --- | --- |
| C7 | 0.0386 |
| C8 | 0.0385 |
| C9 | 0.0445 |
| C10 | 0.4296 |
| C11 | 0.0401 |
| C12 | 0.5222 |
| D7 | 0.0392 |
| D8 | 0.5372 |
| D9 | 0.0432 |
| D10 | 0.4377 |
| D11 | 0.0392 |
| D12 | 0.4824 |
| E7 | 0.0408 |
| E8 | 0.5029 |
| E9 | 0.0405 |
| E10 | 0.4918 |
| E11 | 0.0389 |
| E12 | 0.5087 |
| F7 | 0.0414 |
| F8 | 0.2925 |
| F9 | 0.0392 |
| F10 | 0.4378 |
| F11 | 0.0389 |
| F12 | 0.5307 |
| G7 | 0.0387 |
| G8 | 0.0408 |
| G9 | 0.0391 |
| G10 | 0.0495 |
| G11 | 0.4304 |
| G12 | 0.0384 |
| H7 | 0.0392 |
| H8 | 0.0401 |
| H9 | 0.0386 |
| H10 | 0.0474 |
| H11 | 0.4396 |
| H12 | 0.7874 |

Each well position corresponds to a particular antibiotic at a certain concentration according to the plate plan. Addition of the antibiotic legend is depicted in Table 3.

TABLE 3

| Antibiotic | Well | Mean |
| --- | --- | --- |
| No-antibiotic | A7 | 0.6960 |
| Mero-2 | A8 | 0.0388 |
| Levo-4 | A9 | 0.0744 |
| Ceftria-64 | A10 | 0.0385 |
| Pip/Tazo-64,4 | A11 | 0.0477 |
| Tetra-16 | A12 | 0.4550 |
| Nitro-32 | B7 | 0.0387 |
| Mero-4 | B8 | 0.0390 |
| Levo-8 | B9 | 0.0412 |
| Vanco-2 | B10 | 0.4250 |
| Pip/Tazo-128,4 | B11 | 0.0449 |
| Amp-8 | B12 | 0.4880 |
| Nitro-64 | C7 | 0.0386 |
| Mero-8 | C8 | 0.0385 |
| Ceftria-1 | C9 | 0.0445 |
| Ceftria-8 | F9 | 0.0392 |
| Vanco-32 | F10 | 0.4378 |
| Cefox-32 | F11 | 0.0389 |
| TMP/SMX-4,76 | F12 | 0.5307 |
| Cipro-4 | G7 | 0.0387 |
| Levo-1 | G8 | 0.0408 |
| Ceftria-16 | G9 | 0.0391 |
| Pip/Tazo-16,4 | G10 | 0.0495 |
| Tetra-4 | G11 | 0.4304 |
| Vanco-4 | C10 | 0.4296 |
| Cefox-4 | C11 | 0.0401 |
| Amp-16 | C12 | 0.5222 |
| Nitro-128 | D7 | 0.0392 |
| Amp/Sulb-8,4 | D8 | 0.5372 |
| Ceftria-2 | D9 | 0.0432 |
| Vanco-8 | D10 | 0.4377 |

TABLE 3-continued

| Antibiotic | Well | Mean |
|---|---|---|
| Cefox-8 | D11 | 0.0392 |
| Amp-32 | D12 | 0.4824 |
| Cipro-1 | E7 | 0.0408 |
| Amp/Sulb-16,8 | E8 | 0.5029 |
| Ceftria-4 | E9 | 0.0405 |
| Vanco-16 | E10 | 0.4918 |
| Cefox-16 | E11 | 0.0389 |
| TMP/SMX-2,38 | E12 | 0.5087 |
| Cipro-2 | F7 | 0.0414 |
| Amp/Sulb-32,16 | F8 | 0.2925 |
| AB-Blend | G12 | 0.0384 |
| Mero-1 | H7 | 0.0392 |
| Levo-2 | H8 | 0.0401 |
| Ceftria-32 | H9 | 0.0386 |
| Pip/Tazo-32,4 | H10 | 0.0474 |
| Tetra-8 | H11 | 0.4396 |
| empty | H12 | 0.7874 |

Once the antibiotic legend was placed adjacent to the appropriate well, the data was rearranged by sorting like antibiotics together (Table 4).

TABLE 4

| Antibiotic | Well | Mean |
|---|---|---|
| No-antibiotic | A7 | 0.6960 |
| Nitro-32 | B7 | 0.0387 |
| Nitro-64 | C7 | 0.0386 |
| Nitro-128 | D7 | 0.0392 |
| Cipro-1 | E7 | 0.0408 |
| Cipro-2 | F7 | 0.0414 |
| Cipro-4 | G7 | 0.0387 |
| Mero-1 | H7 | 0.0392 |
| Mero-2 | A8 | 0.0388 |
| Mero-4 | B8 | 0.0390 |
| Mero-8 | C8 | 0.0385 |
| Amp/Sulb-8,4 | D8 | 0.5372 |
| Amp/Sulb-16,8 | E8 | 0.5029 |
| Amp/Sulb-32,16 | F8 | 0.2925 |
| Levo-1 | G8 | 0.0408 |
| Levo-2 | H8 | 0.0401 |
| Levo-4 | A9 | 0.0744 |
| Levo-8 | B9 | 0.0412 |
| Ceftria-1 | C9 | 0.0445 |
| Ceftria-2 | D9 | 0.0432 |
| Ceftria-4 | E9 | 0.0405 |
| Ceftria-8 | F9 | 0.0392 |
| Ceftria-16 | G9 | 0.0390 |
| Ceftria-32 | H9 | 0.0386 |
| Ceftria-64 | A10 | 0.0385 |
| Vanco-2 | B10 | 0.4250 |
| Vanco-4 | C10 | 0.4296 |
| Vanco-8 | D10 | 0.4377 |
| Vanco-16 | E10 | 0.4918 |
| Vanco-32 | F10 | 0.4378 |
| Pip/Tazo-16,4 | G10 | 0.0495 |
| Pip/Tazo-32,4 | H10 | 0.0474 |
| Pip/Tazo-64,4 | A11 | 0.0477 |
| Pip/Tazo-128,4 | B11 | 0.0449 |
| Cefox-4 | C11 | 0.0401 |
| Cefox-8 | D11 | 0.0392 |
| Cefox-16 | E11 | 0.0389 |
| Cefox-32 | F11 | 0.0389 |
| Tetra-4 | G11 | 0.4304 |
| Tetra-8 | H11 | 0.4396 |
| Tetra-16 | A12 | 0.4550 |
| Amp-8 | B12 | 0.4880 |
| Amp-16 | C12 | 0.5222 |
| Amp-32 | D12 | 0.4824 |
| TMP/SMX-2,38 | E12 | 0.5087 |
| TMP/SMX-4,76 | F12 | 0.5307 |
| AB-Blend | G12 | 0.0384 |
| empty | H12 | 0.7874 |

The raw data was then "blanked" using the measurement obtained from the AB-Blend well, as depicted in Table 5.

TABLE 5

| Antibiotic | Well | Mean | Blanked |
|---|---|---|---|
| No-antibiotic | A7 | 0.6960 | 0.6576 |
| Nitro-32 | B7 | 0.0387 | 0.0003 |
| Nitro-64 | C7 | 0.0386 | 0.0002 |
| Nitro-128 | D7 | 0.0392 | 0.0008 |
| Cipro-1 | E7 | 0.0408 | 0.0024 |
| Cipro-2 | F7 | 0.0414 | 0.0030 |
| Cipro-4 | G7 | 0.0387 | 0.0003 |
| Mero-1 | H7 | 0.0392 | 0.0008 |
| Mero-2 | A8 | 0.0388 | 0.0004 |
| Mero-4 | B8 | 0.0390 | 0.0006 |
| Mero-8 | C8 | 0.0385 | 0.0001 |
| Amp/Sulb-8,4 | D8 | 0.5372 | 0.4988 |
| Amp/Sulb-16,8 | E8 | 0.5029 | 0.4646 |
| Amp/Sulb-32,16 | F8 | 0.2925 | 0.2541 |
| Levo-1 | G8 | 0.0408 | 0.0024 |
| Levo-2 | H8 | 0.0401 | 0.0017 |
| Levo-4 | A9 | 0.0744 | 0.0360 |
| Levo-8 | B9 | 0.0412 | 0.0028 |
| Ceftria-1 | C9 | 0.0445 | 0.0061 |
| Ceftria-2 | D9 | 0.0432 | 0.0048 |
| Ceftria-4 | E9 | 0.0405 | 0.0021 |
| Ceftria-8 | F9 | 0.0392 | 0.0008 |
| Ceftria-16 | G9 | 0.0391 | 0.0007 |
| Ceftria-32 | H9 | 0.0386 | 0.0002 |
| Ceftria-64 | A10 | 0.0385 | 0.0001 |
| Vanco-2 | B10 | 0.4250 | 0.3866 |
| Vanco-4 | C10 | 0.4296 | 0.3912 |
| Vanco-8 | D10 | 0.4377 | 0.3993 |
| Vanco-16 | E10 | 0.4918 | 0.4534 |
| Vanco-32 | F10 | 0.4378 | 0.3994 |
| Pip/Tazo-16,4 | G10 | 0.0495 | 0.0111 |
| Pip/Tazo-32,4 | H10 | 0.0474 | 0.0090 |
| Pip/Tazo-64,4 | A11 | 0.0477 | 0.0093 |
| Pip/Tazo-128,4 | B11 | 0.0449 | 0.0065 |
| Cefox-4 | C11 | 0.0401 | 0.0017 |
| Cefox-8 | D11 | 0.0392 | 0.0008 |
| Cefox-16 | E11 | 0.0389 | 0.0005 |
| Cefox-32 | F11 | 0.0389 | 0.0005 |
| Tetra-4 | G11 | 0.4304 | 0.3920 |
| Tetra-8 | H11 | 0.4396 | 0.4012 |
| Tetra-16 | A12 | 0.4550 | 0.4166 |
| Amp-8 | B12 | 0.4880 | 0.4496 |
| Amp-16 | C12 | 0.5222 | 0.4838 |
| Amp-32 | D12 | 0.4824 | 0.4440 |
| TMP/SMX-2,38 | E12 | 0.5087 | 0.4703 |
| TMP/SMX-4,76 | F12 | 0.5307 | 0.4923 |
| AB-Blend | G12 | 0.0384 | 0 |
| empty | H12 | 0.7874 | 0.7490 |

To determine whether bacterial organisms present in the patient samples were resistant or sensitive to a particular antibiotic at a certain concentration, blanked OD readings were compared to a threshold $OD_{600}$ of 0.025 (Table 6). Any OD measurement greater than or equal to this threshold was designated Resistant (R) meaning bacterial organisms present in patient sample were resistant to that particular antibiotic at that certain concentration. Any OD measurement less than this threshold was designated Sensitive (S) meaning bacterial organisms present in patient sample were sensitive to that particular antibiotic at that certain concentration.

TABLE 6

| Antibiotic | Well | Mean | Blanked | Result |
|---|---|---|---|---|
| No-antibiotic | A7 | 0.6960 | 0.6576 | R |
| Nitro-32 | B7 | 0.0387 | 0.0003 | S |
| Nitro-64 | C7 | 0.0386 | 0.0002 | S |
| Nitro-128 | D7 | 0.0392 | 0.0008 | S |

TABLE 6-continued

| Antibiotic | Well | Mean | Blanked | Result |
|---|---|---|---|---|
| Cipro-1 | E7 | 0.0408 | 0.0024 | S |
| Cipro-2 | F7 | 0.0414 | 0.0030 | S |
| Cipro-4 | G7 | 0.0387 | 0.0003 | S |
| Mero-1 | H7 | 0.0392 | 0.0008 | S |
| Mero-2 | A8 | 0.0388 | 0.0004 | S |
| Mero-4 | B8 | 0.0390 | 0.0006 | S |
| Mero-8 | C8 | 0.0385 | 0.0001 | S |
| Amp/Sulb-8,4 | D8 | 0.5372 | 0.4988 | R |
| Amp/Sulb-16,8 | E8 | 0.5029 | 0.4646 | R |
| Amp/Sulb-32,16 | F8 | 0.2925 | 0.2541 | R |
| Levo-1 | G8 | 0.0408 | 0.0024 | S |
| Levo-2 | H8 | 0.0401 | 0.0017 | S |
| Levo-4 | A9 | 0.0744 | 0.0360 | R |
| Levo-8 | B9 | 0.0412 | 0.0028 | S |
| Ceftria-1 | C9 | 0.0445 | 0.0061 | S |
| Ceftria-2 | D9 | 0.0432 | 0.0048 | S |
| Ceftria-4 | E9 | 0.0405 | 0.0021 | S |
| Ceftria-8 | F9 | 0.0392 | 0.0008 | S |
| Ceftria-16 | G9 | 0.0391 | 0.0007 | S |
| Ceftria-32 | H9 | 0.0386 | 0.0002 | S |
| Ceftria-64 | A10 | 0.0385 | 0.0001 | S |
| Vanco-2 | B10 | 0.4250 | 0.3866 | R |
| Vanco-4 | C10 | 0.4296 | 0.3912 | R |
| Vanco-8 | D10 | 0.4377 | 0.3993 | R |
| Vanco-16 | E10 | 0.4918 | 0.4534 | R |
| Vanco-32 | F10 | 0.4378 | 0.3994 | R |
| Pip/Tazo-16,4 | G10 | 0.0495 | 0.0111 | S |
| Pip/Tazo-32,4 | H10 | 0.0474 | 0.0090 | S |
| Pip/Tazo-64,4 | A11 | 0.0477 | 0.0093 | S |
| Pip/Tazo-128,4 | B11 | 0.0449 | 0.0065 | S |
| Cefox-4 | C11 | 0.0401 | 0.0017 | S |
| Cefox-8 | D11 | 0.0392 | 0.0008 | S |
| Cefox-16 | E11 | 0.0389 | 0.0005 | S |
| Cefox-32 | F11 | 0.0389 | 0.0005 | S |
| Tetra-4 | G11 | 0.4304 | 0.3920 | R |
| Tetra-8 | H11 | 0.4396 | 0.4012 | R |
| Tetra-16 | A12 | 0.4550 | 0.4166 | R |
| Amp-8 | B12 | 0.4880 | 0.4496 | R |
| Amp-16 | C12 | 0.5222 | 0.4838 | R |
| Amp-32 | D12 | 0.4824 | 0.4440 | R |
| TMP/SMX-2,38 | E12 | 0.5087 | 0.4703 | R |
| TMP/SMX-4,76 | F12 | 0.5307 | 0.4923 | R |
| AB-Blend | G12 | 0.0384 | 0 | S |
| empty | H12 | 0.7874 | 0.7490 | R |

In this example, the sample contains bacteria sensitive to nitrofurantoin, ciprofloxacin, meropenem, ceftriaxone, piperacillin/tazobactam, and cefoxitin. The results for levo are equivocal.

The MIC for each drug can then be provided. The minimum inhibitory concentration (MIC) is the minimum test antibiotic concentration to which the sample is sensitive. An exemplary MIC determination for meropenem based on the results above is depicted in Table 7.

TABLE 7

| Mero [1] | Mero [2] | Mero [4] | Mero [8] | MIC | Interpretation |
|---|---|---|---|---|---|
| S | S | S | S | <= 1 | S |
| R | S | S | S | <= 2 | I |
| R | R | S | S | <= 4 | I |
| R | R | R | S | <= 8 | I |
| R | R | R | R | >= 8 | R |

Example 3. Validation of ABR Assay Utilizing Agar Containing Growth Medium

Accuracy

Accuracy was assessed by comparing the antibiotic resistance results of the test method compared to those obtained for mixed and isolated cultures evaluated by the antibiotic-agar method. A total of 19 bacterial pools (pools consist of 2-4 organisms), 17 isolated organisms, and 9 routinely processed urine samples were tested for resistance to 12 antibiotics. Accuracy was assessed in regards to Specificity (True Negatives), Sensitivity (True Positives), and Overall Accuracy (All Samples). The assay showed good accuracy in all three categories (Table 8).

TABLE 8

|  | % Accuracy |
|---|---|
| Overall Accuracy | 96% |
| Specificity | 95% |
| Sensitivity | 96% |

Precision

Inter-assay precision was evaluated by testing three samples from the "Accuracy" sample set over three days. Intra-assay precision was evaluated by testing each of these samples in triplicate in one batch. Precision for each sample was assessed by determining the consensus result of all 5 replicates and then counting the number of replicates that match the consensus. This number was then divided by the sum of all measurements (sum of measurements for all drugs) to determine the % precision. The overall precision was calculated by dividing the sum of all correct matches by the total number of measurements from all samples. The assay demonstrated very good precision (Table 9).

TABLE 9

|  | All Precision Samples |
|---|---|
| Total Matched | 643 |
| Total Measurements | 690 |
| Match | 93% |

Analytical Sensitivity

Analytic sensitivity, or the limit of detection (LOD), was assessed by determined the lowest bacterial concentration that yielded accurate results. In certain cases, bacterial concentrations lower than 10,000 cells/mL are not considered positive for UTI and therefore the lowest concentration tested was 10,000 cells/mL. Consistent results (>96%) correlation to the consensus results were obtained at the lowest bacterial concentrations tested. The LOD of this assay was 10,000 cells/mL. Note, the present invention is not limited to a concentration of 10,000 cells/mL.

Analytical Specificity

The analytic specificity of this assay was assessed by testing samples at bacterial concentrations of 100,000,000 cells/mL. Such concentrations are not typically observed in routine UTI patient samples but were achieved in saturated overnight bacterial cultures. Assessment of analytic measurement range (AMR) was then performed by testing three samples from the "Accuracy" sample set each diluted as follows: 100,000,000 cells/mL, 1,000,000 cells/mL, 100,000 cells/mL and 10,000 cells/mL. Consistent results (>94%) correlation to the consensus results were obtained at all bacterial concentrations tested. The assay is specific at bacterial concentration up to 100,000,000 cells/mL. The present invention is not limited to a concentration of 10,000 cells/mL.

Example 4. Antibiotic Resistance (ABR) Assay Utilizing Liquid Growth Medium

Urine samples suitable for processing with this assay are collected, transported, and stored using BD Vacutainer tubes or other suitable leak-proof sterile containers. Urine samples may be held at room temperature for 48 hours before test results are compromised.

Antibiotics not received in ready-made solutions were dissolved in appropriate solvents and according to their individual solubility to 50× the concentration desired in the assay and stored as antibiotic stocks. Antibiotic stocks are stored at 2-8° C. and protected from direct sunlight. Prepared antibiotic stock solutions were aliquoted into a 96-deep well plate (ThermoFisher Scientific) to form a 50× Antibiotic Source Plate and then diluted 1:5 to form a 10× Antibiotic Source Plate, as shown in FIG. 12 where each well is identified by antibiotic name and concentration (μg/mL; 10× final concentration). Antibiotics included in this assay were amoxicillin, clavulanate, ampicillin, sulbactam, cefaclor, cefazolin, cefepime, cefoxitin, ceftazidime, ceftriaxone, ciprofloxacin, gentamicin, levofloxacin, meropenem, nitrofurantoin, piperacillin, tazobactam, tetracycline, trimethoprim, sulfamethoxazole, and vancomycin, either singly or in combination. One well was assigned sodium azide to ensure no bacterial growth would be observed in that well.

Twenty microliters of each antibiotic solution were aliquoted into the pre-determined wells of a 96-well microplate (VIS 96/F-PS, Eppendorf) from the 10× Antibiotic Source Plate to create ABR testing plates for inoculation. These ABR testing plates were allowed to sit for up to 24 hours before use at 2-8° C. in the dark.

At the time of testing, urine samples were centrifuged to concentrate any bacterial cells and then mixed with liquid Mueller-Hinton medium and incubated for 6-16 hours at 37° C. After this initial incubation, the sample is diluted to 0.5-0.6 McF in saline and then 500 μl of that suspension was added to 29.5 μl of Mueller-Hinton medium. One-hundred and eighty microliters of the diluted sample is then aliquoted to each well of the ABR microplate already containing 10× antibiotic solution, bringing all of the antibiotics to the desired final concentration. The plate is then sealed and incubated for 12-16 hours at 37° C.

After incubation, the plate was removed from the incubator and carefully uncovered and the OD600 was determined for each appropriate well by spectrophotometer. Five separate measurements were taken of each well on a plate and the mean OD600 measurement calculated for each well.

Controls are depicted in Table 10.

TABLE 10

| Control Name | Control Conditions |
| --- | --- |
| No-antibiotic control | Any well containing medium that is not infused with antibiotics to ensure viability of bacterial cells present in patient urine samples and included in each plate. If the no-antibiotic control for any given patient does not yield growth, the sample is repeated on the assay and reported as quantity not sufficient if repeat testing still does not yield satisfactory results. |
| Negative control plate | Microplate containing antibiotic-infused agar medium without addition of patient sample or cultured bacterial organisms to ensure non-contamination of reagents. |
| Na Azide | One or more wells containing a dilute concentration of sodium azide to ensure no bacterial growth will occur. |

Raw data collected from the plate is depicted in Table 11. Data in spreadsheet form was arranged as "Well Position" adjacent to its corresponding "Mean" OD.

TABLE 11

| Well | Mean |
| --- | --- |
| A1 | 0.2217 |
| A2 | 0.0496 |
| A3 | 0.2357 |
| A4 | 0.0421 |
| A5 | 0.0539 |
| A6 | 0.1468 |
| A7 | 0.2457 |
| A8 | 0.0427 |
| B1 | 0.0552 |
| B2 | 0.0413 |
| B3 | 0.2449 |
| B4 | 0.0419 |
| B5 | 0.0417 |
| B6 | 0.0570 |
| B7 | 0.2607 |
| B8 | 0.0419 |
| C1 | 0.0539 |
| C2 | 0.0414 |
| C3 | 0.2356 |
| C4 | 0.2202 |
| C5 | 0.0419 |
| C6 | 0.2416 |
| C7 | 0.2473 |
| C8 | 0.2332 |
| D1 | 0.0441 |
| D2 | 0.1180 |
| D3 | 0.0504 |
| D4 | 0.2288 |
| D5 | 0.0418 |
| D6 | 0.2427 |
| D7 | 0.2437 |
| D8 | 0.0600 |
| E1 | 0.0423 |
| E2 | 0.0436 |
| E3 | 0.0435 |
| E4 | 0.2348 |
| E5 | 0.1209 |
| E6 | 0.2417 |
| E7 | 0.0615 |
| E8 | 0.0457 |
| F1 | 0.2198 |
| F2 | 0.0431 |
| F3 | 0.0425 |
| F4 | 0.2084 |
| F5 | 0.1016 |
| F6 | 0.2404 |
| F7 | 0.0426 |
| F8 | 0.2604 |
| G1 | 0.1928 |
| G2 | 0.0443 |
| G3 | 0.0431 |
| G4 | 0.2224 |
| G5 | 0.2339 |
| G6 | 0.2323 |
| G7 | 0.0418 |
| G8 | 0.2354 |
| H1 | 0.1556 |
| H2 | 0.2485 |
| H3 | 0.0426 |
| H4 | 0.1596 |
| H5 | 0.2090 |

TABLE 11-continued

| Well | Mean |
| --- | --- |
| H6 | 0.2281 |
| H7 | 0.0437 |
| H8 | 0.2446 |

Each well position corresponds to a particular antibiotic at a certain concentration according to the plate plan. Addition of the antibiotic legend is depicted in Table 12.

TABLE 12

| Antibiotic | Well | Mean |
| --- | --- | --- |
| No-Antibiotic | A1 | 0.2217 |
| Mero-8 | A2 | 0.0496 |
| Ceftriaxone-4 | A3 | 0.2357 |
| Pip/Tazo-16,4 | A4 | 0.0421 |
| Tetra-16 | A5 | 0.0539 |
| Cefazolin-16 | A6 | 0.1468 |
| Ceftazidime-4 | A7 | 0.2457 |
| No-Antibiotic | A8 | 0.0427 |
| Nitro-32 | B1 | 0.0552 |
| Amp/Sulb-8,4 | B2 | 0.0413 |
| Ceftriaxone-8 | B3 | 0.2449 |
| Pip/Tazo-128,4 | B4 | 0.0419 |
| Amp-8 | B5 | 0.0417 |
| Cefazolin-32 | B6 | 0.0570 |
| Ceftazidime-8 | B7 | 0.2607 |
| No-Antibiotic | B8 | 0.0419 |
| Nitro-128 | C1 | 0.0539 |
| Amp/Suib-32,16 | C2 | 0.0414 |
| Ceftriaxone-64 | C3 | 0.2356 |
| Cefoxitin-4 | C4 | 0.2202 |
| Amp-16 | C5 | 0.0419 |
| Cefepime-1 | C6 | 0.2416 |
| Ceftazidime-16 | C7 | 0.2473 |
| Cefaclor-8 | C8 | 0.2332 |
| Cipro-1 | D1 | 0.0441 |
| Levo-1 | D2 | 0.1180 |
| Vanco-1 | D3 | 0.0504 |
| Cefoxitin-8 | D4 | 0.2288 |
| Amp-32 | D5 | 0.0418 |
| Cefepime-2 | D6 | 0.2427 |
| Ceftazidime-32 | D7 | 0.2437 |
| Cefaclor-32 | D8 | 0.0600 |
| Cipro-4 | E1 | 0.0423 |
| Levo-2 | E2 | 0.0436 |
| Vanco-2 | E3 | 0.0435 |
| Cefoxitin-32 | E4 | 0.2348 |
| TMP/SMX-2,38 | E5 | 0.1209 |
| Cefepime-4 | E6 | 0.2417 |
| Gentamicin-4 | E7 | 0.0615 |
| Na Azide | E8 | 0.0457 |
| Mero-1 | F1 | 0.2198 |
| Levo-4 | F2 | 0.0431 |
| Vanco-4 | F3 | 0.0425 |
| Tetra-2 | F4 | 0.2084 |
| TMP/SMX-4,76 | F5 | 0.1016 |
| Cefepime-8 | F6 | 0.2404 |
| Gentamicin-16 | F7 | 0.0426 |
| No-Antibiotic | F8 | 0.2604 |
| Mero-2 | G1 | 0.1928 |
| Levo-8 | G2 | 0.0443 |
| Vanco-16 | G3 | 0.0431 |
| Tetra-4 | G4 | 0.2224 |
| Cefazolin-2 | G5 | 0.2339 |
| Cefepime-16 | G6 | 0.2323 |
| Amox/Clav-8,4 | G7 | 0.0418 |
| No-Antibiotic | G8 | 0.2354 |
| Mero-4 | H1 | 0.1556 |
| Ceftriaxone-1 | H2 | 0.2485 |
| Vanco-32 | H3 | 0.0426 |
| Tetra-8 | H4 | 0.1596 |
| Cefazolin-8 | H5 | 0.2090 |
| Cefepime-32 | H6 | 0.2281 |
| Amox/Clav-32,16 | H7 | 0.0437 |
| No-Antibiotic | H8 | 0.2446 |

With antibiotic legend placed adjacent to the appropriate well, the data was rearranged by sorting like antibiotics together (Table 13).

TABLE 13

| Antibiotic | Well | Mean |
| --- | --- | --- |
| Na Azide | E8 | 0.0457 |
| No-Antibiotic | A1 | 0.2217 |
| No-Antibiotic | F8 | 0.2604 |
| No-Antibiotic | G8 | 0.2354 |
| No-Antibiotic | H8 | 0.2446 |
| Amox/Clav-8,4 | G7 | 0.0418 |
| Amox/Clav-32,16 | H7 | 0.0437 |
| Amp-8 | B5 | 0.0417 |
| Amp-16 | C5 | 0.0419 |
| Amp-32 | D5 | 0.0418 |
| Amp/Sulb-8,4 | B2 | 0.0413 |
| Amp/Sulb-32,16 | C2 | 0.0414 |
| Cefaclor-8 | C8 | 0.2332 |
| Cefaclor-32 | D8 | 0.0600 |
| Cefazolin-2 | G5 | 0.2339 |
| Cefazolin-8 | H5 | 0.2090 |
| Cefazolin-16 | A6 | 0.1468 |
| Cefazolin-32 | B6 | 0.0570 |
| Cefepime-1 | C6 | 0.2416 |
| Cefepime-2 | D6 | 0.2427 |
| Cefepime-4 | E6 | 0.2417 |
| Cefepime-8 | F6 | 0.2404 |
| Cefepime-16 | G6 | 0.2323 |
| Cefepime-32 | H6 | 0.2281 |
| Cefoxitin-4 | C4 | 0.2202 |
| Cefoxitin-8 | D4 | 0.2288 |
| Cefoxitin-32 | E4 | 0.2348 |
| Ceftazidime-4 | A7 | 0.2457 |
| Ceftazidime-8 | B7 | 0.2607 |
| Ceftazidime-16 | C7 | 0.2473 |
| Ceftazidime-32 | D7 | 0.2437 |
| Ceftriaxone-1 | H2 | 0.2485 |
| Ceftriaxone-4 | A3 | 0 2357 |
| Ceftriaxone-8 | B3 | 0 2449 |
| Ceftriaxone-64 | C3 | 0.2356 |
| Cipro-1 | D1 | 0.0441 |
| Cipro-4 | E1 | 0.0423 |
| No-Antibiotic | A8 | 0 0427 |
| No-Antibiotic | B8 | 0.0419 |
| Gentamicin-4 | E7 | 0.0615 |
| Gentamicin-16 | F7 | 0.0426 |
| Levo-1 | D2 | 0.1180 |
| Levo-2 | E2 | 0.0436 |
| Levo-4 | F2 | 0.0431 |
| Levo-8 | G2 | 0.0443 |
| Mero-1 | F1 | 0.2198 |
| Mero-2 | G1 | 0.1928 |
| Mero-4 | H1 | 0.1556 |
| Mero-8 | A2 | 0.0496 |
| Nitro-32 | B1 | 0.0552 |
| Nitro-128 | C1 | 0.0539 |
| Pip/Tazo-16,4 | A4 | 0.0421 |
| Pip/Tazo-128,4 | B4 | 0.0419 |
| Tetra-2 | F4 | 0.2084 |
| Tetra-4 | G4 | 0.2224 |
| Tetra-8 | H4 | 0.1596 |
| Tetra-16 | A5 | 0.0539 |
| TMP/SMX-2,38 | E5 | 0.1209 |
| TMP/SMX-4,76 | F5 | 0.1016 |
| Vanco-1 | D3 | 0.0504 |
| Vanco-2 | E3 | 0.0435 |
| Vanco-4 | F3 | 0.0425 |
| Vanco-16 | G3 | 0.0431 |
| Vanco-32 | H3 | 0.0426 |

The raw data was then "blanked" using the measurement obtained from the Na-Azide well, as depicted in Table 14.

TABLE 14

| Antibiotic | Well | Mean | Blanked |
|---|---|---|---|
| Na Azide | E8 | 0.0457 | 0 |
| No-Antibiotic | A1 | 0.2217 | 0.1760 |
| No-Antibiotic | F8 | 0.2604 | 0.2147 |
| No-Antibiotic | G8 | 0.2354 | 0.1897 |
| No-Antibiotic | H8 | 0.2446 | 0.1989 |
| Amox/Clav-8,4 | G7 | 0.0418 | −0.0039 |
| Amox/Clav-32,16 | H7 | 0.0437 | −0.0020 |
| Amp-8 | B5 | 0.0417 | −0.0040 |
| Amp-16 | C5 | 0.0419 | −0.0038 |
| Amp-32 | D5 | 0.0418 | −0.0039 |
| Amp/Sulb-8,4 | B2 | 0.0413 | −0.0044 |
| Amp/Sulb-32,16 | C2 | 0.0414 | −0.0043 |
| Cefaclor-8 | C8 | 0.2332 | 0.1875 |
| Cefaclor-32 | D8 | 0.0600 | 0.0143 |
| Cefazolin-2 | G5 | 0.2339 | 0.1882 |
| Cefazolin-8 | H5 | 0.2090 | 0.1633 |
| Cefazolin-16 | A6 | 0.1468 | 0.1011 |
| Cefazolin-32 | B6 | 0.0570 | 0.0113 |
| Cefepime-1 | C6 | 0.2416 | 0.1959 |
| Cefepime-2 | D6 | 0.2427 | 0.1970 |
| Cefepime-4 | E6 | 0.2417 | 0.1960 |
| Cefepime-8 | F6 | 0.2404 | 0.1947 |
| Cefepime-16 | G6 | 0.2323 | 0.1866 |
| Cefepime-32 | H6 | 0.2281 | 0.1824 |
| Cefoxitin-4 | C4 | 0.2202 | 0.1745 |
| Cefoxitin-8 | D4 | 0.2288 | 0.1831 |
| Cefoxitin-32 | E4 | 0.2348 | 0.1891 |
| Ceftazidime-4 | A7 | 0.2457 | 0.2000 |
| Ceftazidime-8 | B7 | 0.2607 | 0.2150 |
| Ceftazidime-16 | C7 | 0.2473 | 0.2016 |
| Ceftazidime-32 | D7 | 0.2437 | 0.1980 |
| Ceftriaxone-1 | H2 | 0.2485 | 0.2028 |
| Ceftriaxone-4 | A3 | 0.2357 | 0.1900 |
| Ceftriaxone-8 | B3 | 0.2449 | 0.1992 |
| Ceftriaxone-64 | C3 | 0.2356 | 0.1899 |
| Cipro-1 | D1 | 0.0441 | −0.0016 |
| Cipro-4 | E1 | 0.0423 | −0.0034 |
| No-Antibiotic | A8 | 0.0427 | −0.0030 |
| No-Antibiotic | B8 | 0.0419 | −0.0038 |
| Gentamicin-4 | E7 | 0.0615 | 0.0158 |
| Gentamicin-16 | F7 | 0.0426 | −0.0031 |
| Levo-1 | D2 | 0.1180 | 0.0723 |
| Levo-2 | E2 | 0.0436 | −0.0021 |
| Levo-4 | F2 | 0.0431 | −0.0026 |
| Levo-8 | G2 | 0.0443 | −0.0014 |
| Mero-1 | F1 | 0.2198 | 0.1741 |
| Mero-2 | G1 | 0.1928 | 0.1471 |
| Mero-4 | H1 | 0.1556 | 0.1099 |
| Mero-8 | A2 | 0.0496 | 0.0039 |
| Nitro-32 | B1 | 0.0552 | 0.0095 |
| Nitro-128 | C1 | 0.0539 | 0.0082 |
| Pip/Tazo-16,4 | A4 | 0.0421 | −0.0036 |
| Pip/Tazo-128,4 | B4 | 0.0419 | −0.0038 |
| Tetra-2 | F4 | 0.2084 | 0.1627 |
| Tetra-4 | G4 | 0.2224 | 0.1767 |
| Tetra-8 | H4 | 0.1596 | 0.1139 |
| Tetra-16 | A5 | 0.0539 | 0.0082 |
| TMP/SMX-2,38 | E5 | 0.1209 | 0.0752 |
| TMP/SMX-4,76 | F5 | 0.1016 | 0.0559 |
| Vanco-1 | D3 | 0.0504 | 0.0047 |
| Vanco-2 | E3 | 0.0435 | −0.0022 |
| Vanco-4 | F3 | 0.0425 | −0.0032 |
| Vanco-16 | G3 | 0.0431 | −0.0026 |
| Vanco-32 | H3 | 0.0426 | −0.0031 |

To determine whether bacterial organisms present in the patient samples were resistant or sensitive to a particular antibiotic at a certain concentration, blanked OD readings were compared to a threshold $OD_{600}$ of 0.065 (Table 15). An OD measurement greater than or equal to this threshold was designated Resistant (R) meaning bacterial organisms present in patient sample were resistant to that particular antibiotic at that certain concentration. Any OD measurement less than this threshold was designated Sensitive (S) meaning bacterial organisms present in patient sample were sensitive to that particular antibiotic at that certain concentration.

TABLE 15

| Antibiotic | Well | Mean | Blanked | Result |
|---|---|---|---|---|
| Na Azide | E8 | 0.0457 | 0 | S |
| No-Antibiotic | A1 | 0.2217 | 0.1760 | R |
| No-Antibiotic | F8 | 0.2604 | 0.2147 | R |
| No-Antibiotic | G8 | 0.2354 | 0.1897 | R |
| No-Antibiotic | H8 | 0.2446 | 0.1989 | R |
| Amox/Clav-8,4 | G7 | 0.0418 | −0.0039 | S |
| Amox/Clav-32,16 | H7 | 0.0437 | −0.0020 | S |
| Amp-8 | B5 | 0.0417 | −0.0040 | S |
| Amp-16 | C5 | 0.0419 | −0.0038 | S |
| Amp-32 | D5 | 0.0418 | −0.0039 | S |
| Amp/Sulb-8,4 | B2 | 0.0413 | −0.0044 | S |
| Amp/Sulb-32,16 | C2 | 0.0414 | −0.0043 | S |
| Cefaclor-8 | C8 | 0.2332 | 0.1875 | R |
| Cefaclor-32 | D8 | 0.0600 | 0.0143 | S |
| Cefazolin-2 | G5 | 0.2339 | 0.1882 | R |
| Cefazolin-8 | H5 | 0.2090 | 0.1633 | R |
| Cefazolin-16 | A6 | 0.1468 | 0.1011 | R |
| Cefazolin-32 | B6 | 0.0570 | 0.0113 | S |
| Cefepime-1 | C6 | 0.2416 | 0.1959 | R |
| Cefepime-2 | D6 | 0.2427 | 0.1970 | R |
| Cefepime-4 | E6 | 0.2417 | 0.1960 | R |
| Cefepime-8 | F6 | 0.2404 | 0.1947 | R |
| Cefepime-16 | G6 | 0.2323 | 0.1866 | R |
| Cefepime-32 | H6 | 0.2281 | 0.1824 | R |
| Cefoxitin-4 | C4 | 0.2202 | 0.1745 | R |
| Cefoxitin-8 | D4 | 0.2288 | 0.1831 | R |
| Cefoxitin-32 | E4 | 0.2348 | 0.1891 | R |
| Ceftazidime-4 | A7 | 0.2457 | 0.2000 | R |
| Ceftazidime-8 | B7 | 0.2607 | 0.2150 | R |
| Ceftazidime-16 | C7 | 0.2473 | 0.2016 | R |
| Ceftazidime-32 | D7 | 0.2437 | 0.1980 | R |
| Ceftriaxone-1 | H2 | 0.2485 | 0.2028 | R |
| Ceftriaxone-4 | A3 | 0.2357 | 0.1900 | R |
| Ceftriaxone-8 | B3 | 0.2449 | 0.1992 | R |
| Ceftriaxone-64 | C3 | 0.2356 | 0.1899 | R |
| Cipro-1 | D1 | 0.0441 | −0.0016 | S |
| Cipro-4 | E1 | 0.0423 | −0.0034 | S |
| No-Antibiotic | A8 | 0.0427 | −0.0030 | S |
| No-Antibiotic | B8 | 0.0419 | −0.0038 | S |
| Gentamicin-4 | E7 | 0.0615 | 0.0158 | S |
| Gentamicin-16 | F7 | 0.0426 | −0.0031 | S |
| Levo-1 | D2 | 0.1180 | 0.0723 | R |
| Levo-2 | E2 | 0.0436 | −0.0021 | S |
| Levo-4 | F2 | 0.0431 | −0.0026 | S |
| Levo-8 | G2 | 0.0443 | −0.0014 | S |
| Mero-1 | F1 | 0.2198 | 0.1741 | R |
| Mero-2 | G1 | 0.1928 | 0.1471 | R |
| Mero-4 | H1 | 0.1556 | 0.1099 | R |
| Mero-8 | A2 | 0.0496 | 0.0039 | S |
| Nitro-32 | B1 | 0.0552 | 0.0095 | S |
| Nitro-128 | C1 | 0.0539 | 0.0082 | S |
| Pip/Tazo-16,4 | A4 | 0.0421 | −0.0036 | S |
| Pip/Tazo-128,4 | B4 | 0.0419 | −0.0038 | S |
| Tetra-2 | F4 | 0.2084 | 0.1627 | R |
| Tetra-4 | G4 | 0.2224 | 0.1767 | R |
| Tetra-8 | H4 | 0.1596 | 0.1139 | R |
| Tetra-16 | A5 | 0.0539 | 0.0082 | S |
| TMP/SMX-2,38 | E5 | 0.1209 | 0.0752 | R |
| TMP/SMX-4,76 | F5 | 0.1016 | 0.0559 | S |
| Vanco-1 | D3 | 0.0504 | 0.0047 | S |
| Vanco-2 | E3 | 0.0435 | −0.0022 | S |
| Vanco-4 | F3 | 0.0425 | −0.0032 | S |
| Vanco-16 | G3 | 0.0431 | −0.0026 | S |
| Vanco-32 | H3 | 0.0426 | −0.0031 | S |

In this example, the sample contains bacteria sensitive to amoxicillin/clavulanate, ampicillin, ampicillin/sulbactam, ciprofloxacin, gentamicin, levofloxacin, nitrofurantoin, piperacillin/tazobactam, and vancomycin.

The MIC for each drug can then be provided. The minimum inhibitory concentration (MIC) is the minimum test antibiotic concentration to which the sample is sensitive. An exemplary MIC determination for meropenem based on the results above is depicted in Table 16.

TABLE 16

| Mero [1] | Mero [2] | Mero [4] | Mero [8] | MIC | Interpretation |
|---|---|---|---|---|---|
| S | S | S | S | <= 1 | S |
| R | S | S | S | <= 2 | I |
| R | R | S | S | <= 4 | I |
| R | R | R | S | <= 8 | I |
| R | R | R | R | >= 8 | R |

Example 5. Validation of ABR Assay Utilizing Liquid Growth Medium

Accuracy

Accuracy was assessed by comparing the antibiotic resistance results of the test method to a consensus of results obtained by standard reference methods. A total of 15 isolated organisms, and 20 routinely processed patient urine samples were tested for resistance to 18 antibiotics, each tested at multiple concentrations for a total of 57 antibiotic concentrations. Accuracy was assessed regarding Specificity (True Negatives), Sensitivity (True Positives), and overall Accuracy (all samples). The assay showed good accuracy in all three categories (Table 17).

TABLE 17

|  | % Accuracy |
|---|---|
| Overall Accuracy | 96% |
| Specificity | 95% |
| Sensitivity | 97% |

Precision

Inter-Assay precision was evaluated by testing five samples over three different days. Intra-Assay precision was evaluated by testing the same five samples in triplicate in a single day. Percent concordance was calculated to measure the precision of results obtained by this assay. The assay demonstrated very good precision (Table 18).

TABLE 18

| | Precision | |
|---|---|---|
| Description | Intra-Assay | Inter-Assay |
| Total # of Matches | 841 | 1388 |
| Total # of Measurements | 855 | 1425 |
| % Concordance | 98% | 97% |

Analytic

Analytic Sensitivity

Analytic sensitivity was evaluated by creating a dilution series of *E. coli* and *E. faecalis* with the lowest bacterial concentration at less than 100 cells/mL for each organism. Each dilution level for each isolate was tested to show reproducibility of results down to the lowest concentration. 98% correlation was observed across all dilution levels for both isolates, indicating the limit of detection (LOD) of this assay is less than 100 cells/ml.

Analytic Specificity

Analytic specificity was evaluated in the context of inhibitory effect of overloading the assay with too many bacterial cells. Lower accuracy (due to false-resistant results) was observed for samples inoculated at high bacterial concentration. This indicates that all samples must be diluted to the specified cell density post pre-culture and before ABR inoculation.

Pre-Culture Duration Determination

This assay utilizes a pre-culture step prior to introducing samples to antibiotics. The duration of this pre-culture incubation was tested at 6 and 16 hours for 2 isolates (*E. coli* and *E. faecalis*). Good accuracy for each isolate was observed after both 6 and 16 hour pre-culture incubations, indicating a pre-culture window of 6 to 16 hours for this assay. Results displayed below in Table 19.

TABLE 19

| Description | # Results | % Accuracy |
|---|---|---|
| Total # of Matches | 81 | 98% |
| Total # of Measurements | 83 | |

Incubation

Incubation Duration Determination

Once samples are introduced to antibiotics, they are incubated for 12 to 16 hours. This incubation length was determined by obtaining OD measurements for Precision samples after 12 and 16 hours of incubation. Good percent concordance was observed for all samples across within a 12 to 16 hour incubation window (Table 20).

TABLE 20

| Description | # Targets | % Concordance |
|---|---|---|
| Total # of Matches | 2758 | 97% |
| Total # of Measurements | 2850 | |

Bacterial Growth

Bacterial Growth Confirmation

To confirm turbidity (high OD measurements) are due to bacterial growth, DNA was extracted from wells corresponding to Sensitive and Resistant results and tested for pathogen identification by PCR. Identification results confirm Resistant (turbid) wells contained significantly higher bacterial concentration than Sensitive (clear) wells (Table 21).

TABLE 21

| Overall (Cells/mL) | |
|---|---|
| Resistant | 5,170,897,798 |
| Sensitive | 1,341,116 |
| Fold-Diff | 3,856 |

Unless otherwise indicated, all numbers expressing quantities of ingredients, properties such as molecular weight, reaction conditions, and so forth used in the specification and claims are to be understood as being modified in all instances by the term "about." As used herein the terms "about" and "approximately" means within 10 to 15%, preferably within 5 to 10%. Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

Furthermore, numerous references have been made to patents and printed publications throughout this specification. Each of the above-cited references and printed publications are individually incorporated herein by reference in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

What is claimed is:

1. A method for treating a patient having or suspected of having a polymicrobial infection comprising a combination of *Escherichia coli* (*E. coli*) and coagulase-negative *Staphylococcus* (CoNS), the method comprising:
   a. detecting the presence of both *E. coli* and CoNS in a source of the infection obtained from the patient; and
   b. administering to the patient a therapeutically effective amount of an antibiotic selected from the group consisting of: (i) a combination of amoxicillin and clavulanate; (ii) ceftriaxone; (iii) tetracycline or doxycycline; and (iv) a combination of trimethoprim and sulfamethoxazole; wherein the *E. coli* and CoNS together have a decreased odds of resistance to one or more of the antibiotics, and wherein the antibiotics are effective for killing or inhibiting growth of the *E. coli* and CoNS to treat the polymicrobial infection.

2. The method of claim 1, wherein the *E. coli* and CoNS are detected in the source of the infection without first being isolated.

3. A method for treating a patient having or suspected of having a polymicrobial infection comprising a combination of *Escherichia coli* (*E. coli*) and coagulase-negative *Staphylococcus* (CoNS), the method comprising:
   a. detecting the presence of both *E. coli* and CoNS in a source of the infection obtained from the patient; and
   b. administering to the patient a therapeutically effective amount of an antibiotic selected from the group consisting of: (i) a combination of amoxicillin and clavulanate; and (ii) ceftriaxone;
   wherein the *E. coli* and CoNS together have a decreased odds of resistance to one or more of the antibiotics, and wherein the antibiotics are effective for killing or inhibiting growth of the *E. coli* and CoNS to treat the polymicrobial infection.

4. The method of claim 1, wherein the *E. coli* and CoNS are detected in the source of the infection without first being isolated.

\* \* \* \* \*